(12) United States Patent
Suárez et al.

(10) Patent No.: US 8,859,625 B2
(45) Date of Patent: Oct. 14, 2014

(54) METHODS TO PREPARE PENTA-1,4-DIEN-3-ONES AND SUBSTITUTED CYCLOHEXANONES AND DERIVATIVES WITH ANTITUMORAL AND ANTIPARASITIC PROPERTIES, THE COMPOUNDS AND THEIR USES

(75) Inventors: José Agustin Quincoces Suárez, Sao Paulo (BR); Durvanei Augusto Maria, Sao Paulo (BR); Daniela Goncales Rando, Sao Paulo (BR); Clizete Aparecida Sbravate Martins, Sao Bernardo do Campo (BR); Paulo Celso Pardi, Praia Grande (BR); Pamela Oliveira De Souza, Sao Paulo (BR)

(73) Assignee: Universidade Bandeirante de Sao Paulo-Academia, Paulista Anchieta S/C Ltda, Sao Paulo (BR)

( * ) Notice: Subject to any disclaimer, the term of this patent is extended or adjusted under 35 U.S.C. 154(b) by 1290 days.

(21) Appl. No.: 12/307,669

(22) PCT Filed: Jul. 6, 2007

(86) PCT No.: PCT/BR2007/000175
§ 371 (c)(1),
(2), (4) Date: Oct. 5, 2009

(87) PCT Pub. No.: WO2008/003155
PCT Pub. Date: Jan. 10, 2008

(65) Prior Publication Data
US 2010/0029763 A1     Feb. 4, 2010

(30) Foreign Application Priority Data
Jul. 6, 2006     (BR) .................................... 0602640

(51) Int. Cl.
*A61K 31/12*     (2006.01)
*C07C 45/00*     (2006.01)

(52) U.S. Cl.
USPC ............................ 514/679; 514/678; 568/315

(58) Field of Classification Search
USPC .................................. 514/678, 679; 568/315
See application file for complete search history.

(56) References Cited

U.S. PATENT DOCUMENTS 7,432,401 B2 * 10/2008 Suarez et al. ................. 568/313

FOREIGN PATENT DOCUMENTS

WO     2004047716 A2     6/2004
WO     2006044379 A2     4/2006

OTHER PUBLICATIONS

Stahl et al, Handbook of Pharmaceutical Salts, properties, selection, use, 2002, Wiley-Vch, p. 1-7,142-143,162-169,214-215,262-263,266-267,310-321,342-345.*

* cited by examiner

*Primary Examiner* — T. Victor Oh
(74) *Attorney, Agent, or Firm* — Nixon Peabody LLP

(57) ABSTRACT

The present invention refers to new derivatives of the penta-1,4-dien-3-ones, as well as their processes of preparation. These compounds present strong antitumoral activity and promising antiparasitic action, behaving as almost atoxic by laboratory assays and also by hystopathologic studies. The present invention refers also to a pharmaceutical composition including the referred compounds, method of treatment for cancer and parasitic diseases.

10 Claims, 19 Drawing Sheets

METHODS TO PREPARE PENTA-1,4-DIEN-3-ONES AND SUBSTITUTED CYCLOHEXANONES AND DERIVATIVES WITH ANTITUMORAL AND ANTIPARASITIC PROPERTIES, THE COMPOUNDS AND THEIR USES

CROSS REFERENCE TO RELATED APPLICATION(S)

This application is a 35 U.S.C. §371 National Phase Entry Application from PCT/BR2007/000175, filed Jul. 6, 2007, and designating the United States. This application also claims the benefit of Brazilian Application No. PI-0602640-0, filed Jul. 6, 2006, the disclosure of which is incorporated herein in its entirety by reference.

FIELD OF THE INVENTION

The present invention refers to methods to prepare the 1,5-bis(aryl)penta-1,4-dien-3-one derivatives, covering from its synthetic methods of preparation and purification up to their in vivo biological applications as antitumoral agents and in vitro applications as antiparasite agents, among others.

The present invention refers also to a chemical composition that presents pharmaceutical applicability, which includes the referred compounds, to treat cancer and parasitosis.

DESCRIPTION OF THE PRIOR ART

H. van der Goot et al. (Eur. J. Med. Chem. 32, 625-630, 1997) have obtained 1,5-Diaryl-1,4-pentadien-3-ones and their cyclic analogues that show antioxidant properties. The cyclic compounds were synthesized by the reaction of the substituted aldehydes with cyclohexanone and/or cyclopentanone in the presence of hydrochloric acid.

M. Artico et al., in their article published in the J. Med. Chem. (v. 41, 3948-3960, 1998), report the preparation of 2,6-Bis(3,4-dihydroxy-benzyliden)cyclohexanones, 3,5-Bis (3,4-dihydroxy-benzylidene)piperidin-4-ones, and 3,5-Bis (3,4-dihydroxy-benzyliden)tetrahydro-piran-4-ones with anti-HIV-1 properties in studies performed with MT-4 cells.

Afterwards, Buolomwini and Assefa, in their article published in J. Med. Chem. (45, 841-852, 2002), proved the anti-HIV action of 2,5-Bis(3,4-dihydroxy-benzyliden)cyclopentanone and 3,5-Bis(3,4-dihydroxy-benzyliden)tetrahydro-thiopiran-4-one.

In 2004 and 2005, Youssef et al. (Arch. Pharm. Med. Chem. 337, 42-54, 2004; Arch. Pharm. Chem. Life Sci. 338, 181-189, 2005) developed the synthesis of substituted 2,7-bis (benzylidene)cycloheptanones and of 3,5-Bis(benzylidene)-N-alkyl-4-piperidones from the reaction of the correspondent substituted aldehydes and cycloheptanone or 4-piperididone in acidic medium, in that these compounds have shown an antioxidant and chemopreventive anticancer activity.

In the year of 2004, the article published in the journal Bioorganic & Medicinal Chemistry (12, 3871-3883, 2005) includes a list of products assessed for antitumoral antiangiogenic properties, derived from 2,6-Bis((4-hydroxy-3-methoxy-phenyl)-methyliden)-cyclohexanone. The compound 3,5-Bis(2-fluoro-benzylidene)-4-oxo-piperidine acetate stands out as the most active compound.

Recently, a new method to obtain 1,5-bis(4-hydroxy-3-methoxy-phenyl)penta-1,4-dien-3-one and its derivatives and their in vitro antitumoral properties, by an ultrasound technique (J. Quincoces et al. "New Method for the Preparation of 1,5-Bis(4-Hydroxy-3-methoxy-phenyl)penta-1,4-dien-3-one and Derivatives with antitumoral properties": PI 0207141-0; PCT: May 28, 2005) was published. The synthetic derivatives of 1,5-bis(4-hydroxy-3-methoxy-phenyl) penta-1,4-dien-3-one with antitumoral properties, protected by the present patent claim, are shown in the following Figure:

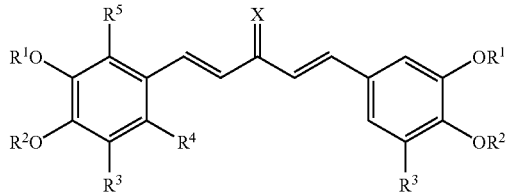

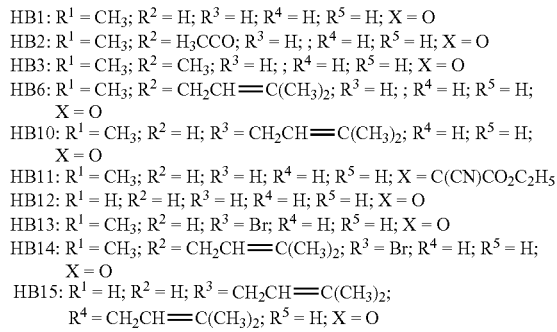

HB1: $R^1 = CH_3$; $R^2 = H$; $R^3 = H$; $R^4 = H$; $R^5 = H$; $X = O$
HB2: $R^1 = CH_3$; $R^2 = H_3CCO$; $R^3 = H$; ; $R^4 = H$; $R^5 = H$; $X = O$
HB3: $R^1 = CH_3$; $R^2 = CH_3$; $R^3 = H$; ; $R^4 = H$; $R^5 = H$; $X = O$
HB6: $R^1 = CH_3$; $R^2 = CH_2CH\!=\!C(CH_3)_2$; $R^3 = H$; ; $R^4 = H$; $R^5 = H$; $X = O$
HB10: $R^1 = CH_3$; $R^2 = H$; $R^3 = CH_2CH\!=\!C(CH_3)_2$; $R^4 = H$; $R^5 = H$; $X = O$
HB11: $R^1 = CH_3$; $R^2 = H$; $R^3 = H$; $R^4 = H$; $R^5 = H$; $X = C(CN)CO_2C_2H_5$
HB12: $R^1 = H$; $R^2 = H$; $R^3 = H$; $R^4 = H$; $R^5 = H$; $X = O$
HB13: $R^1 = CH_3$; $R^2 = H$; $R^3 = Br$; $R^4 = H$; $R^5 = H$; $X = O$
HB14: $R^1 = CH_3$; $R^2 = CH_2CH\!=\!C(CH_3)_2$; $R^3 = Br$; $R^4 = H$; $R^5 = H$; $X = O$
HB15: $R^1 = H$; $R^2 = H$; $R^3 = CH_2CH\!=\!C(CH_3)_2$; $R^4 = CH_2CH\!=\!C(CH_3)_2$; $R^5 = H$; $X = O$

In addition, in this present patent claim the in vivo toxicological results of such compounds, such as the $LD_{50}$ (50% lethal dose) values, were protected.

It should be also considered that, due to the presence of phenolic hydroxy groups, such compounds may be handled as mono and disalts. These referred derivatives were not described until now in the literature either synthetic or biologically.

The synthesis or biological property assessment of some products deriving from an O-alkylation of the previous analogues was not previously reported in the literature.

Substituted 4-nitro-3,5-diaryl-cyclohexanones were obtained by Thayumanavan and collaborators, in 2002, by Diels-Alder amino-catalyzed reactions between α,β-insaturated ketones and nitrodienophiles (Tetrahedron Letters 43, 3817-3820, 2002). Through this approach, such compounds are generated at good yields (yields up to 87%), but modest enantioselectivity. The applied methodology, however, offers the advantage of not requiring the isolation of the 2-amino-1,3-butadien intermediary, which is generated in situ and, therefore, the substituted 4-nitro-3,5-diaryl-cyclohexanones are prepared as a single step.

Crawshaw and collaborators (Tetrahedron Letters, 38, 7115-7118, 1997) have shown that 4-nitro-3,5-diaryl-cyclohexanones may be obtained by the reaction of maleimides and nitrostyrenes performed on a solid phase. By means of this methodology, products are obtained at moderate yields (37 to 87%), but in high purity degrees (~90%).

In the last decades, Padmavathi and collaborators (Indian Journal of Chemistry, 31B, 7, 407-410, 1992) have been actively searching for Michael additions to the double bonds to obtain cyclic adducts, among which are the 1,1-dicyano-3-methyl-6-aryl-4-oxocyclohexane derivatives. V. Padmavathi et al. report in their article, published in the Journal Heterocyclic Chem., 42, 797-802, 2005, the synthesis of 1,1-Dicyano-3-methyl-2-phenyl-6-aryl-4-oxocyclohexanes through Michael addition of malononitrile on 1,5-diaryl-2- methyl-1,4-penta-dien-3-one in the presence of Triton B, using these compounds as intermediates in the process to obtain Spiro Heterocycles.

In 1998, Rowland et al. have studied the stereochemistry of C-1 and C-2 positions for diaryl-substituted cyclohexanones and have shown the interconversion capacity from trans isomers into cis isomers under basic conditions (Journal of Organic Chemistry, 63, 4359-4365, 1998).

The biological applications of the compounds above described and of interest for this patent comprise antitumoral and antiparasite applications.

Cancer or neoplasia is the name given to a collective of more than 100 diseases characterized by the uncontrolled growth of abnormal cells that may affect almost any tissue of the body. It affects more than 11 million people every year and it is responsible for 7 million deaths per year, which may be translated from a statistical point of view as 12.5% of world deaths (World Health Organization. Cancer. Available at the Internet: http://www.who.int/cancer/en Access on 22 Sep. 2005).

Melanomas are neoplasias that arise on the skin; however, they may also proceed from mucosal surfaces or from other sites of migration from cells of the neural crest and may occur in the eyes (intraocular melanoma), meninges, gastrointestinal tract, and lymphonodi, among other places. The tumor prevails in adults and, in more than half of the cases, in apparently normal skin locations and those exposed to sunlight. In men, the tumor is more common in the trunk, head, or neck. In women, it is more common appears in the distal third of the inferior members. In dark skin people, melanoma is generally located in the subungual region, palmar or plantar. The most common symptoms are itching, change of surface texture, local bleeding, and even pain. Melanomas are severe cutaneous tumors. Progression of a malignant cancer depends on the success of a series of events. These events are continuous growth of the tumoral cells, their ability to avoid apoptosis and to overcome inhibitory growth signals, in addition to develop a response and to maintain an angiogenic response, to invade neighbor tissues, and move to distant organs (metastasis). Invasion and metastasis are important aspects of tumor progression. Both processes seem to result from a local balance between regulators and effectors, with cooperation among adhesion molecules, cytoskeleton elements, proteases to degrade the extracellular matrix, and regulatory molecules.

Among the most used therapeutical drugs are doxorubicin, paclitaxel, and etoposide. The following Table lists some values for posology, 50% lethal dose, and side effects for some of the most used antitumoral drugs.

As observed in the Table below, these drugs present a series of disadvantages, such as relatively high effective doses, low therapeutical index, in addition to undesirable and frequent side effects that undermine patient's condition or that require hospital admission highly decreasing patient's life quality.

As for parasitic diseases, leishmaniasis, for example, is a pathological condition caused by a protozoary infection of the *Leishmania* gender and that is until today a disease of great social and economics importance, ranking likely second among the parasitosis caused by protozoary, probably second in importance right after malaria. According to the reports from the World Health Organization UNDP/World Bank/WHO—*Special program for research and training in tropical diseases* (Available in the internet, http://who.ch/programmes/tdr/workplan/leishman.htm, access on Sep. 22, 2005), in 1996, 88 countries had been affected by the disease, with 12 million people infected and around 350 million at risk.

| ANTITUMORAL DRUG | POSOLOGY | 50% LETHAL DOSE | SIDE EFFECTS |
|---|---|---|---|
| Doxorubicin | 60 to 75 mg/m$^2$ | 20 mg/kg | Cardiac toxicity, headache, vomiting, nausea, myelosuppression |
| Taxol | 135 to 175 mg/m$^2$ | 31.8 mg/kg | Allergic reactions, bone marrow suppression, muscle pain, nausea, vomiting, diarrhea, hair lost |
| Etoposide | 50 to 100 mg/m$^2$ | 59 mg/kg | Bone marrow suppression, neurotoxicity, hair loss, stomatitis, anorexia. |

The most employed drugs to treat this disease are the pentavalent antimony drugs, such as N-methyl glucamine antimoniate and sodium stibogluconate. In general, both drugs possess good curative index for leishmaniasis for both cutaneous and visceral; however, by the parenteral administration route, parasite resistance and drug toxicity represent the main problems found in the treatment with such drugs (Rev. Soc. Bras. Med. Trop. 33(6), 535-543, 2000).

Other drugs, such as amphotericin B, pentamidine, mefloquine, and miltefosine are also employed in the therapeutics for these parasitic diseases, although with lower efficacy than that of antimony drugs and the fact that they are employed in cases of parasite resistance or patient intolerance (Trop. Dis. Hyg. 8, 319-342, 2002).

The following Table lists some of the drugs used to treat leishmaniasis, their posology, side effects, and some comments on their use limitations.

| Drug | Posology | Use limitations | Side Effects |
|---|---|---|---|
| N-methyl glucamine antimoniate | 20 mg/kg/day (20-28 days) | Endovenous or intramuscular administration, very long periods of treatment, parasite resistance already described. | Arthralgia, myalgia, pancreatitis, headache, nervousness, pyrogen shock, edema, renal failure, and arrhythmias. |

-continued

| Drug | Posology | Use limitations | Side Effects |
|---|---|---|---|
| Pentamidine | 4 mg/kg/3× week (5-25 weeks) | Low curative power, high toxicity, it should not be administered to hypersensitive patients or those suffering from renal failure. | Hypotension, syncope, extended hypoglycemia, tachycardia, and others; arrhythmias, renal failure, and pancreatitis. |
| Amphotericin B | 0.2 mg/kg/day (3-12 weeks) | High toxicity, not to be administered to patients suffering from renal or heart pathologies, toxic for vascular epithelium cells. | phlebitis, headache, fever, chills, asthenia, arthralgia and myalgia, vomiting and hypotension, cardiovascular and lung alterations, bone marrow depression, hyperkalemia |

As shown on the Table above, the several limitations to use the drugs available to treat leishmaniasis are related to their high toxicity that causes several and severe side effects and adverse reactions in a wide spectrum of intensity and severity leading, several times, to treatment discontinuation. Other factors that difficult or make the use of classic drugs impracticable are: inconvenience of the routes of administration, always parenteral, which discourages patient commitment/or requires an inevitable hospitalization; the refractory nature of some cases to the treatment; drug resistance developed by some species or parasite isolates; and the long term required for the treatment, frequently discontinued by the patient.

The present invention refers also to the use of the above mentioned drugs to treat human and animal neoplasias and parasitic disease, to the determination of more appropriate therapeutic regimens to each type of disease, to the determination of synergetic effect of the association among two or more of such compounds, to the determination of the mode of action of the active compounds, toxicity, and other pharmacological parameters to the referred families of compounds that appear as more auspicious than those drugs presently employed in the therapeutics, for the diseases above mentioned and for other correlated diseases.

B—Infiltrate nodular tumor mass with extensive necrosis areas.

Figure 27:

FIG. 27—Photomicrography of melanoma dorsal tumor implanted in C57BL/6J mice after 14 days of treatment with Miglyol 810® diluent administered by the intraperitoneal route.

A—Nodular, pigmented dorsal tumor.

B—Nodular, pigmented, vascularized (*) dorsal tumor with great areas of necrosis.

Figure 28:
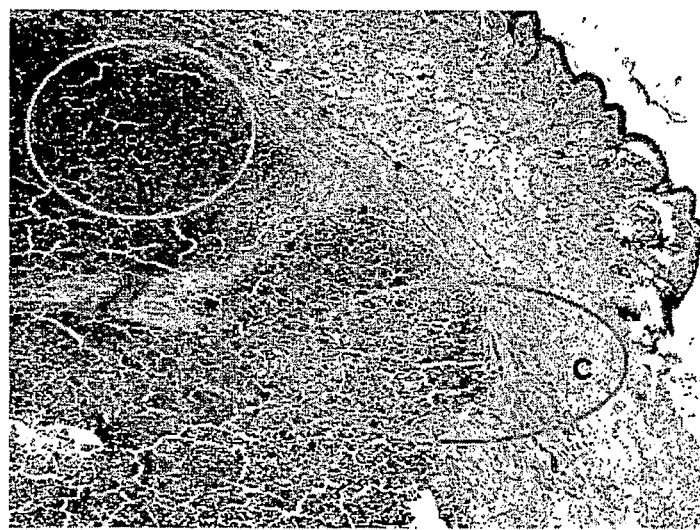

FIG. 28—Photomicrography of melanoma dorsal tumor implanted in C57BL/6J mice after 14 days of treatment with Miglyol 810® diluent administered by the intraperitoneal route.

C—Nodular, pigmented dorsal tumor with absence of intra- and peritumoral infiltrate inflammatory leukocytes.

D—Nodular, pigmented, vascularized (*) dorsal tumor with great necrosis areas.

Figure 29:
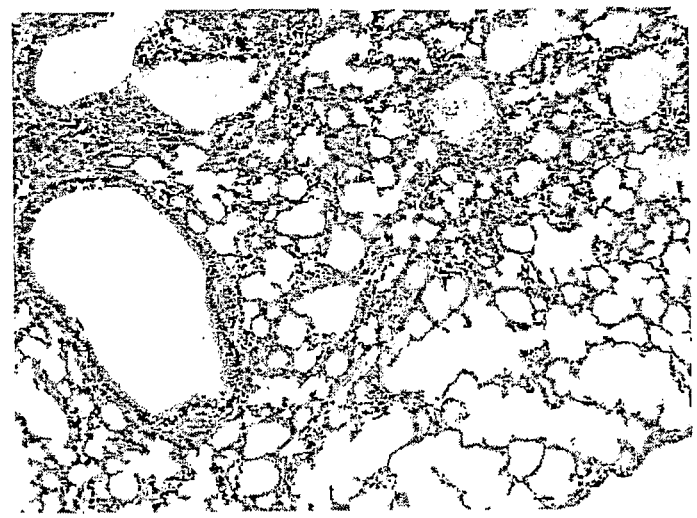

FIG. 29—Photomicrography of lung parenchyma of C57BL/6J mice bearing dorsal melanoma tumor from the group treated with the HB-1 compound in Miglyol810®.

Figure 30:
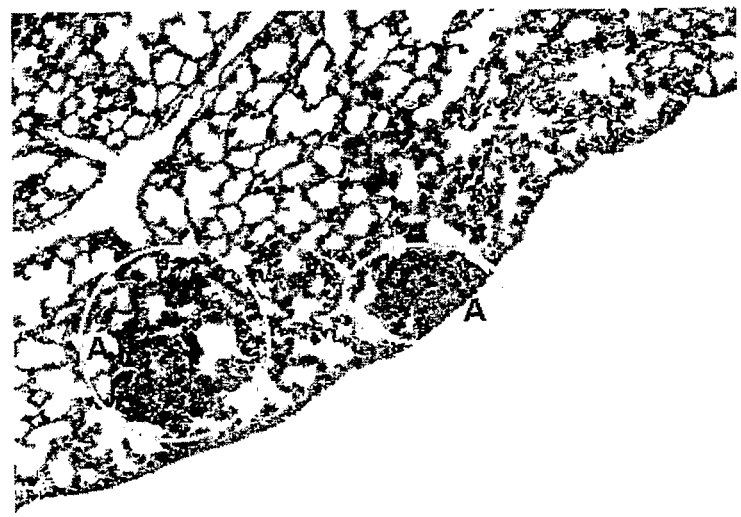

FIG. 30—Photomicrography of lung parenchyma of C57BL/6J mice bearing dorsal melanoma tumor from the group treated Miglyol810®.

Figure 31:
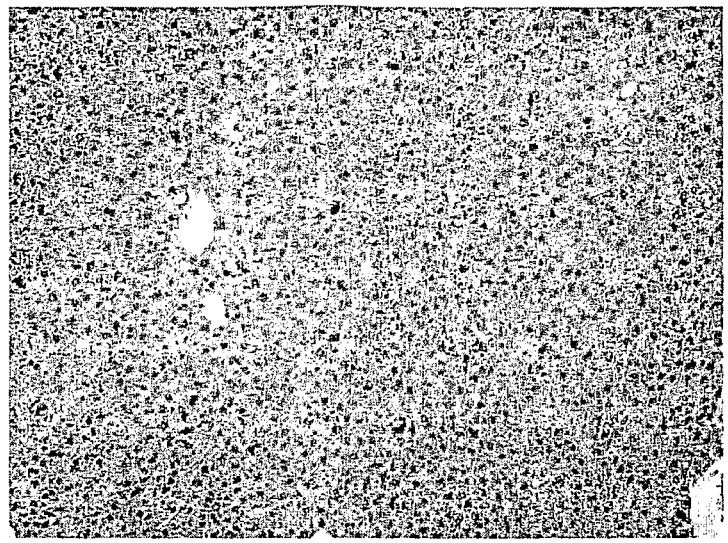

FIG. 31—Photomicrography of a liver parenchyma section showing well-preserved hepatocytes, well-defined lobules, and radial pattern of the trabecula.

Figure 32:
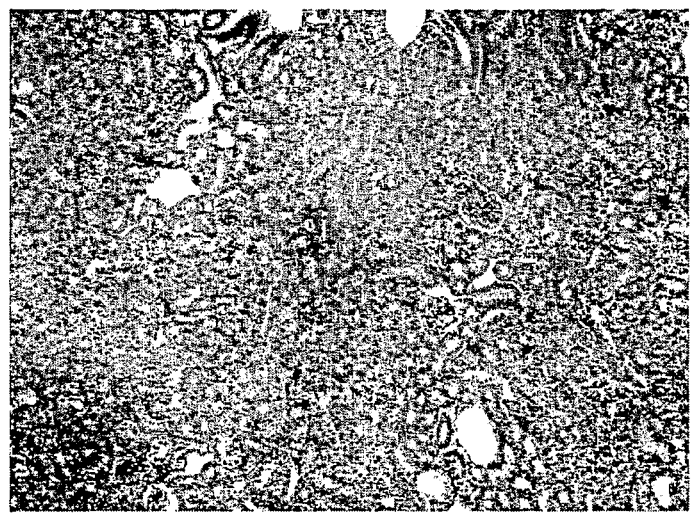

FIG. 32—Photomicrography of a renal parenchyma, demonstrating typical and well-preserved renal corpuscles, distal and proximal convoluted tubules also well-preserved, without any structural change.

Figure 33:
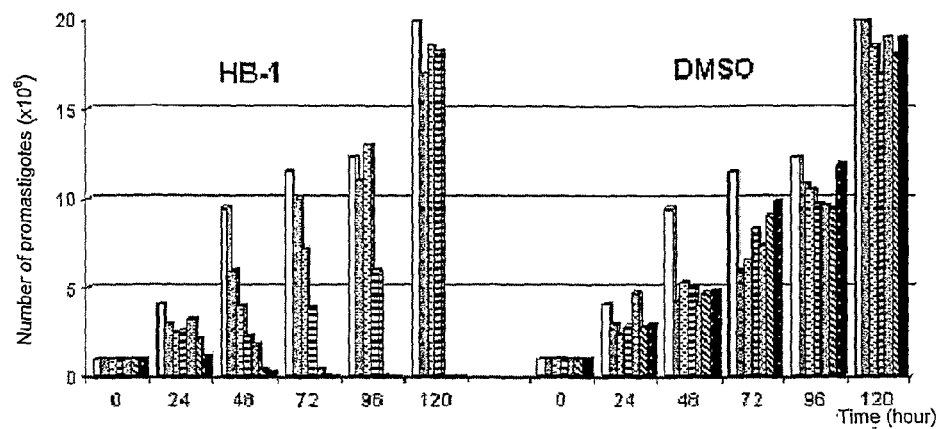

FIG. 33—Effect of HB1 compound on promastigote forms of *Leishmania amazonensis* cultivated in Warren medium.

Figure 34:
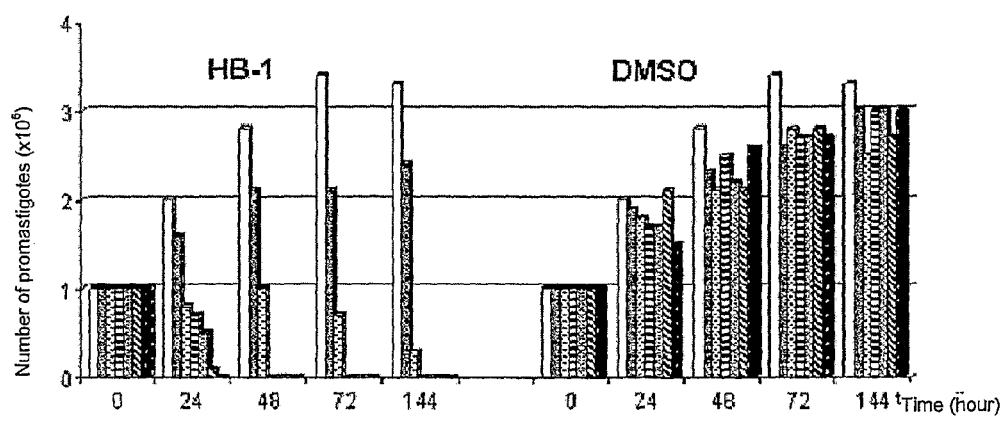

FIG. 34—Effect of HB1 compound on promastigote forms of *Leishmania amazonensis* cultivated in RPMI medium.

Figure 35:
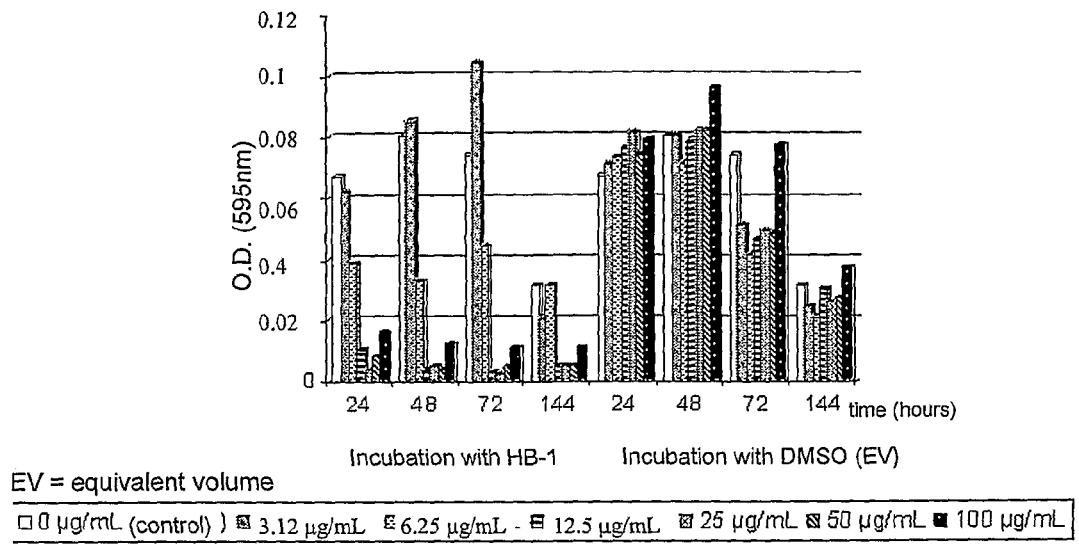

FIG. 35—Viability of promastigote forms of *Leishmania (L) amazonensis* treated with HB-1, in RPMI medium.

Figure 36:
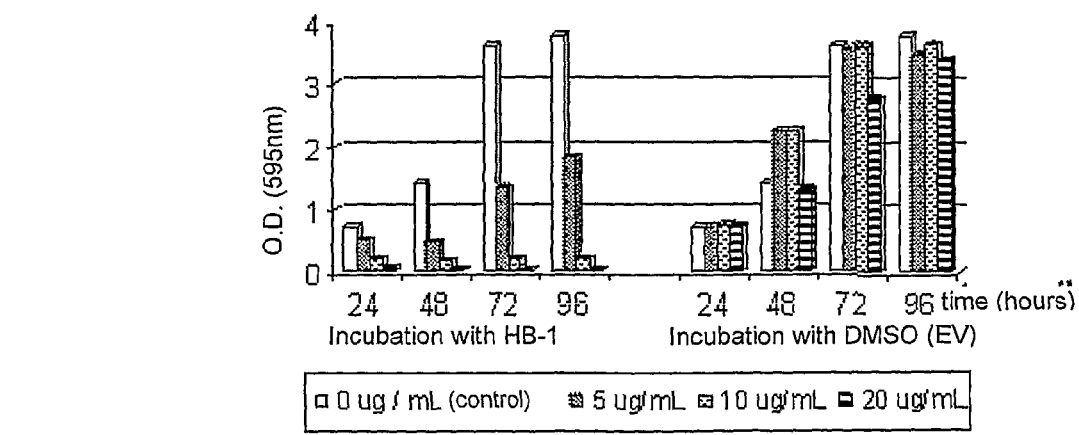

FIG. 36—Effect of HB1 compound on promastigote forms of *Leishmania* (L.C.L. isolated) incubated in Warren medium, in the presence of HB-1.

Figure 37:
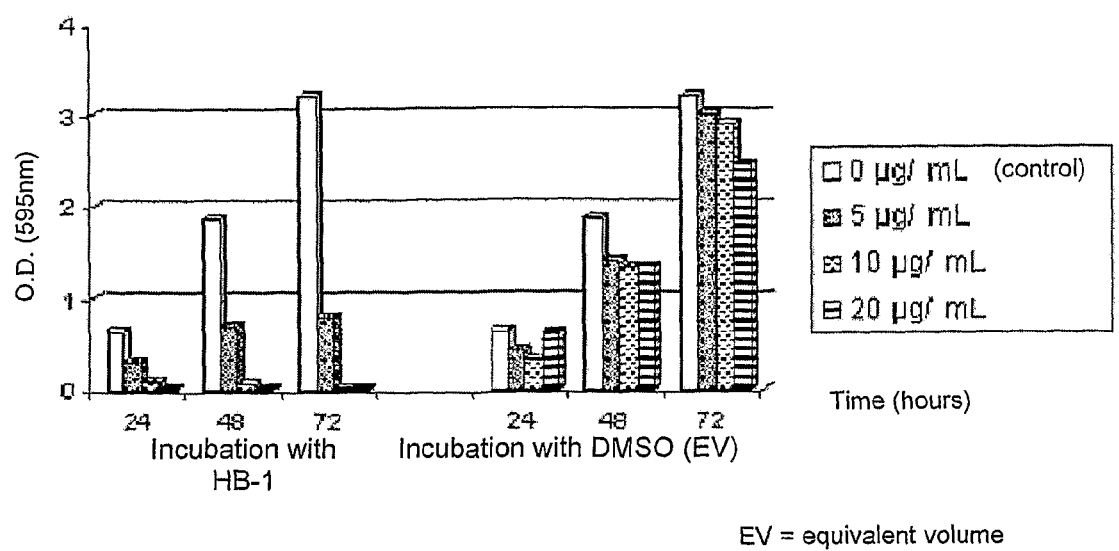

FIG. 37—Effect of HB1 compound on promastigote forms of *Leishmania* (D.C.D. isolated) incubated in Warren medium, in the presence of HB-1.

DETAILED DESCRIPTION OF THE INVENTION

Part 1

Synthesis, Isolation, and Characterization of the Derivatives

The present invention refers to the preparation of 4-[5-(4-hydroxy-3-methoxy-phenyl)-3-oxo-penta-1,4-dienyl]-2-methoxy-phenolates and 3-oxo-penta-1,4-dienyl-bis(2-methoxy-phenolates) from 1,5-bis(4-hydroxy-3-methoxy-phenyl)penta-1,4-dien-3-one in the presence of metallic alkoxide on a 1:1 and 1:2 molar ratio, respectively. Preferably, a 1,5-bis(4-hydroxy-3-methoxy-phenyl)penta-1,4-dien-3-one is put in contact with an alcoholic solution of the respective alkoxide, followed by solvent rotoevaporation until solid constitution. The monosalt and disalt derivatives can be obtained due to the presence of two phenolic groups in the structures and its proportion is controlled by the molar ratio of the reagents. Once obtained, phenolates are passed trough a sieve in order to obtain a fine powder more easily solubilized in water and used in the biological tests described afterwards in this document. Other mono and disalt derivatives of 1,5-bis(4-hydroxy-3-methoxy-phenyl)penta-1,4-dien-3-one with antiparasite and antitumoral properties are shown in the following Figure,

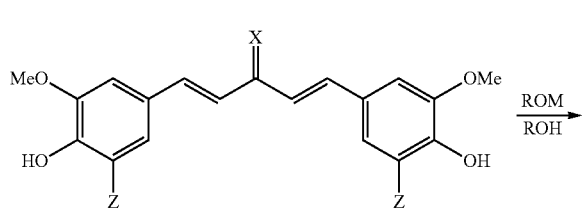

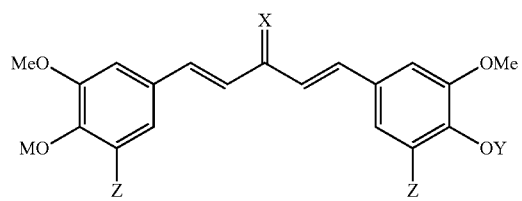

DM1: X = O; Y = Na ou K; Z = H; M = Na; K
DM2: X = O; Y = H; Z = H; M = Na; K
DM3: X = C(CN)$_2$; Y = Na; Z = H; M = Na; K
DM4: X = C(CN)$_2$; Y = H; Z = H; M = Na; K
DM5: X = C(COOCH$_3$)CN; Y = Na; Z = H; M = Na; K
DM6: X = C(COOCH$_3$)CN; Y = H; Z = H; M = Na; K
DM7: X = C(COOEt)CN; Y = Na; Z = H; M = Na; K
DM8: X = C(COOEt)CN; Y = H; Z = H; M = Na; K
DM9: X = O; Y = Na; Z = NO$_2$; M = Na; K
DM10: X = O; Y = H; Z = NO$_2$; M = Na; K
DM11: X = C(CN)$_2$; Y = Na; Z = NO$_2$; M = Na; K
DM12: X = C(CN)$_2$; Y = H; Z = NO$_2$; M = Na; K
DM13: X = C(COOCH$_3$)CN; Y = Na; Z = NO$_2$; M = Na; K
DM14: X = C(COOCH$_3$)CN; Y = H; Z = NO$_2$; M = Na; K
DM15: X = O; Y = Na; Z = NH$_2$; M = Na; K
DM16: X = O; Y = H; Z = NH$_2$; M = Na; K where X may be an oxygen atom, a malononitrile group, or even an alkyl cyanoacetate; Y varies between a hydrogen or a metallic cation stabilizing the compound as a phenoxide ion; Z includes nitro and amino groups in addition to non-substituted compounds in such position (Z=H), and M represents a metallic cation stabilizing the compound as a phenoxide ion.

The present invention also refers to a new process to prepare other 1,5-bis(4-hydroxy-3-methoxy-phenyl)penta-1,4-dien-3-one derivatives with antiparasite and antitumoral properties.

The Figure below describes the new synthesized derivatives of 1,5-bis(4-hydroxy-3-methoxy-phenyl)penta-1,4-dien-3-one with antiparasite and antitumoral properties.

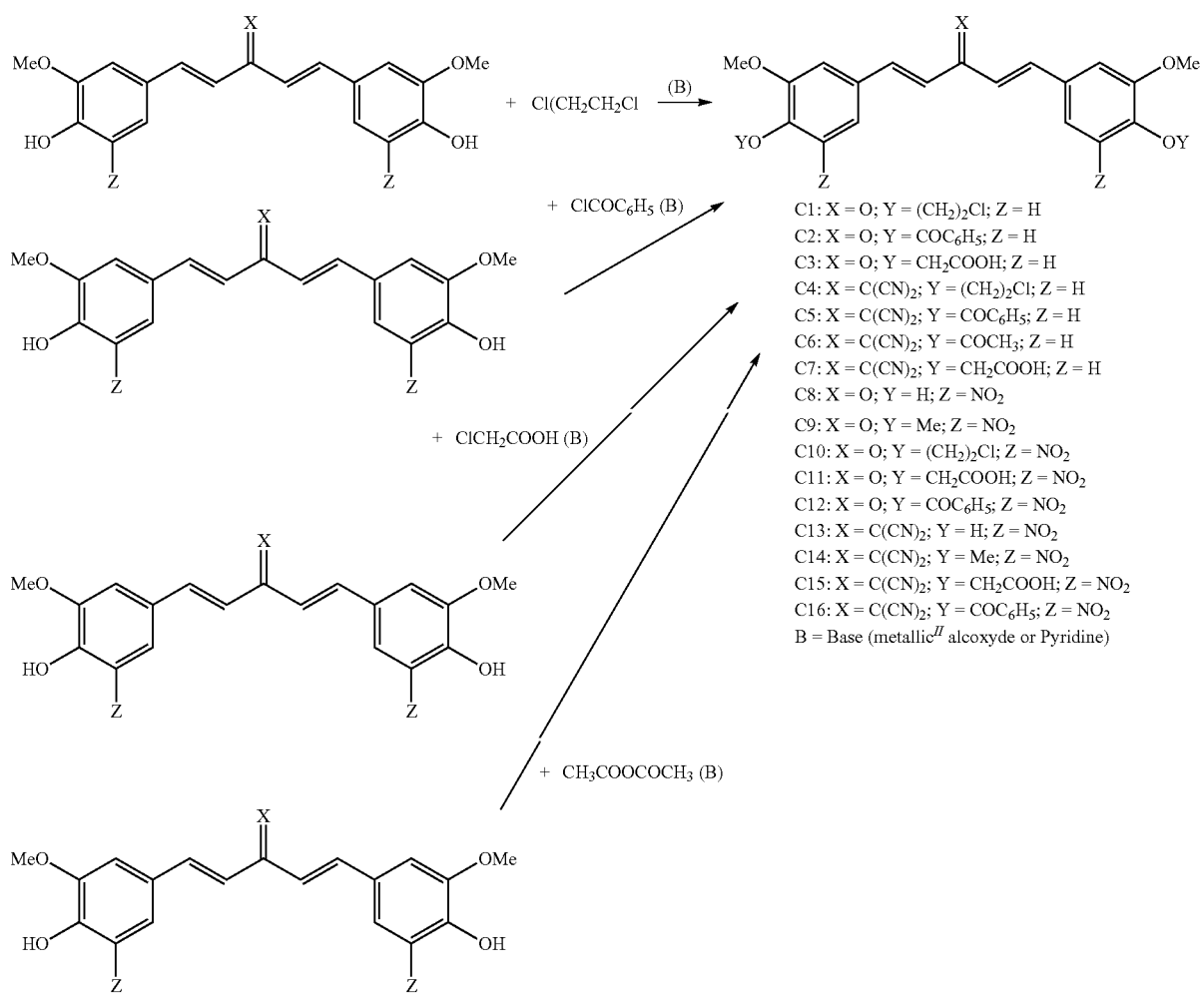

Where X varies from an oxygen and malononitrile, Z consists of a nitro group or a hydrogen atom, and Y consists of groups such as benzoyl, methyl, chloroethyl, acetyl, carboxymethylene, in addition to a hydrogen atom that configures a non-substituted compound.

The same acylated or alkylated pentadienones are also obtained from the correspondent alkylated or acylated substituted aldehydes and ketones under ultrasound irradiation in the range of 25 to 40 KHz in acidic medium, at temperatures varying from 25 to 60° C., let to rest for periods of time that range between 1-7 days, as shown by the Figure below.

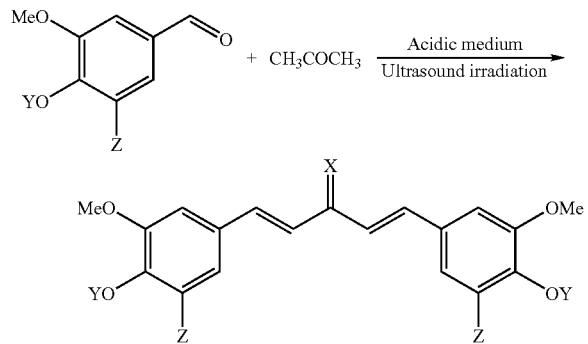

in that X represents oxygen and malonitrile, Z represents a nitro group or a hydrogen atom, Y represents benzoyl, methyl, chloroethyl, acetyl, and carboxymethylene groups and the hydrogen atom that configures the non-substituted compound, leading to the same derivative compounds synthesized from 1,5-bis(4-hydroxy-3-methoxy-phenyl)penta-1,4-dien-3-one, which had been previously identified by its code.

The present invention refers also to a new process to prepare the substituted 4-Nitro-3,5-diaryl-cyclohexanones or substituted, 2,6-diaryl-cyclohexanones, which consists of mixing the substituted 1,5-bis(aryl)penta-1,4-dien-3-ones and nitroalkane or malonic acid derivatives, respectively, under the conditions of Michael addition reaction. Preferably, the substituted 1,5-bis(aryl)penta-1,4-dien-3-ones and nitroalkane or the malonic acid derivatives react at a 1:1 molar ratio, at temperatures that range between 20-60° C., under ultrasound irradiation at a range of 25 to 40 KHz, for a period of time ranging from 1 to 8 hours.

In the next Figure are listed the new cyclohexanones derivatives (substituted 4-Nitro-3,5-diaryl-cyclohexanones and substituted 2,6-diaryl-cyclohexanones) synthesized, which have exhibited antitumoral and antiparasite properties.

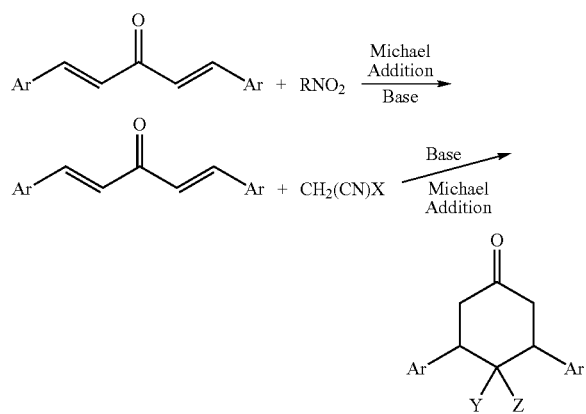

C17: Ar=3,5-di(fur-2-yl); Y=NO₂; Z=H

C18: Ar=3,5-di(fur-2-yl); Y=NO₂; Z=Me

C19: Ar=3,5-diphenyl; Y=NO₂; Z=Me

C20: Ar=3,5-Bis[4-(2chloro-ethoxy)-3-methoxy-phenyl]; Y=NO₂; Z=H

C21: Ar=3,5-Bis[3,4-dimethoxy-phenyl]; Y=NO₂; Z=H

C22: Ar=3,5-Bis[4-carboxymethoxy-3-methoxy-phenyl]; Y=NO₂; Z=H

C23: Ar=3,5-Bis[4-acetoxy-3-methoxy-phenyl]; Y=NO₂; Z=H

C24: Ar=3,5-Bis[4-benzoyloxy-3-methoxy-phenyl]; Y=NO₂; Z=H

C25: Ar=3,5-Bis[3-methoxy-4-(3-methyl-but-2-enyloxy)-phenyl]; Y=NO₂; Z=H

C26: Ar=3,5-Bis[3-methoxy-4-(3-methyl-but-2-enyloxy)-phenyl]; Y=CN; Z=CN

Base=metallic alkoxide or Triton B

R=alkyl groups; X=CN or COOR

Where Ar includes aromatic groups such as 3,4-dimethoxyphenyl; 4-carboxymethoxy-3-methoxy-phenyl; 4-acetoxy-3-methoxy-phenyl; 3-methoxy-4-(3-methyl-but-2-enyloxy)-phenyl; 4-(2-chloro-ethoxy)-3-methoxy-phenyl; 4-benzoyloxy-3-methoxy-phenyl, or aryl and heteroaromatics, such as furan and thiophene, Y being a nitro group or a cyano group, and Z including, in addition to the hydrogen atom, the methyl and cyano groups. As for reagents, R is an alkyl and X alcoxycarbonyl and cyano groups.

The substituted 4-Nitro-3,5-diaryl-cyclohexanones or the substituted 2,6-diaryl-cyclohexanones, in the presence of substituted aldehydes catalyzed in acidic or basic medium are transformed into the substituted 2,6-Dibenzylidene-4-nitro-3,5-diaryl-cyclohexanones or substituted 3,5-Dibenzylidene-2,6-diaryl-cyclohexanones, respectively.

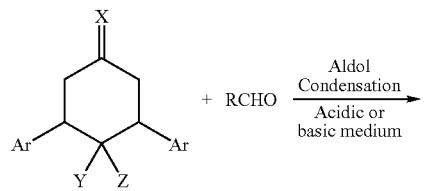

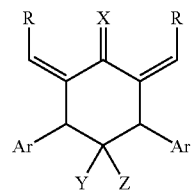

In the Figure above are listed the new synthesized derivatives of the substituted 2,6-Dibenzylidene-4-nitro-3,5-diaryl-cyclohexanones and substituted 3,5-Dibenzylidene-2,6-diaryl-cyclohexanones that exhibit antitumoral and antiparasite properties C27: X=O; Y=NO₂; Z=Me; R=2,6-bis-furan-2-yl-methylene; Ar=3,5-bis(fur-2-yl)

C28: X=O; Y=NO₂; Z=Me; R=2,6-bis-furan-2-il-methylene; Ar=3,5-diphenyl

C29: X=O; Y=NO₂; Z=Me; R=2,6-bis(5-bromum-fur-2-yl)methylene] Ar=3,5-diphenyl

C30: X=O; Y=NO₂; Z=H; R=2,6-bis-furan-2-yl-methylene; Ar=3,5-bis(3,4-dimethoxy-phenyl)

C31: X=O; Y=NO₂; Z=H; R=2,6-bis(3,4-dimethoxy-phenyl); Ar=3,5-bis(3,4-dimethoxy-phenyl)

C32: X=O; Y=NO₂; Z=H; R=2,6-bis-furan-2-yl)methylene; Ar=3,5-bis-[3-methoxy-4-(3-methyl-but-enyloxy)-phenyl]

C33: X=O; Z=H; Y=NO₂; R=2,6-bis(3,4-dimethoxy-phenyl); Ar=3,5-bis-[3-methoxy-4-(3-methoxy-but-2-enyloxy)-phenyl]

C34: X=C(CN)₂; Z=H; Y=NO₂; R=2,6-bis(3,4-dimethoxy-phenyl); Ar=3,5-bis-[3-methoxy-4-(3-methyl-but-2-enyloxy-phenyl]

C35: X=C(CN)₂; Z=H; Y=NO₂; R=2,6-bis-furan-2-yl-methylene; Ar=3,5-bis-[3-methoxy-4-(3-methyl-but-2-enyloxy)-phenyl]

Where X is an atom of oxygen or a C(CN)₂ or a C(CN)COOR group and Z ranges among methyl, hydrogen, or cyano group; Y is constant, such as a nitro or cyano group, and R is 3,4-dimethoxyphenyl; 4-carboxymethoxy-3-methoxy-phenyl; 4-acetoxy-3-methoxy-phenyl; 3-methoxy-4-(3-methyl-but-2-enyloxy)-phenyl; 4-(2-chloro-ethoxy)-3-methoxy-phenyl; 4-benzoyloxy-3-methoxy-phenyl, or aryl and heteroaromatics, such as furan and thiophene.

These inventions may be illustrated by means of the following examples of execution:

Example 1

Preparation of sodium 4-[5-(4-hydroxy-3-methoxy-phenyl)-3-oxo-penta-1,4-dienyl]-2-methoxy-phenolate (codified as DM1)

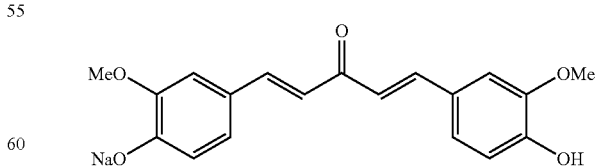

From 1,5-bis(4-hydroxy-3-methoxy-phenyl)penta-1,4-dien-3-one in the presence of metallic alkoxide in a 1:1 molar ratio. Preferably, 1,5-bis(4-hydroxy-3-methoxy-phenyl)penta-1,4-dien-3-one is mixed with an alcoholic solution of the respective alkoxide, followed by solvent rotoevaporation until solid constitution. Monosalt may be obtained with a high yield. Once obtained, the phenolate is passed through a sieve in order to obtain a fine powder more easily solubilized in water and applied to the biological tests further described in this document.

The product shows a dark red colour.
General formula: $C_{19}H_{17}O_5Na$. Molecular weight: 348.
Yield: 90%.
Result from Structural Characterization:
UV-VIS: Maximum absorption 388 nm in water.
Through acidification with hydrochloric acid, the monosalt is transformed into the correspondent 1,5-bis(4-hydroxy-3-methoxy-phenyl)penta-1,4-dien-3-one, which is extracted with ethyl ether or chloroform or ethyl acetate. Results of the structural characterization of the isolated compound are as following:

1,5-Bis-(4-hydroxy-3-methoxy-phenyl)-penta-1,4-dien-3-one, also denominated HB-1.

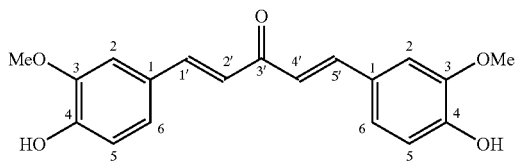 [SMILES: COc1cc(/C=C/C(=O)/C=C/c2ccc(O)c(OC)c2)ccc1O]

General formula: $C_{19}H_{18}O_5$. Molecular weight=326.
Melting point=140° C.
Yield: 92%.
Results from the Quantitative Elementary Analysis:

| Calculation | | Found | |
|---|---|---|---|
| C | 69.94% | C | 69.91% |
| H | 5.52% | H | 5.49% |

Spectroscopic Analyses.
$^1$H-NMR (CDCl$_3$): 7.7 (d, 2H, H-1', H-5'); 7.19 (m, H-2, H-5, H-6); 4.0 (s, 6H, MeO) ppm.
$^{13}$C-NMR (CDCl$_3$): 188 (C-3'); 148 (C-1', C-5'); 146 (C-3); 143 (C-4); 128 (C-2', C-4'); 122.9 (C-1); 116.5 (C-6); 110 (C-2, C-5); 56 (C from the methoxy group) ppm.
IV (film): at 3396 (OH band); 2962 (C sp$^2$H); 2841 (Csp$^3$H); 1587 (C=O conjugate) cm$^{-1}$.
MS (70 eV): 327 (M$^+$+$^+$H); 28 (327.3-299.3), which corresponds to the CO group 32 (M$^+$-295), which corresponds to the methoxy group 15 (203-188), which corresponds to the methyl group.

Example 2

Preparation of disodium 3-oxo-penta-1,4-dienyl-bis(2-methoxy-phenolate) codified as DM2)

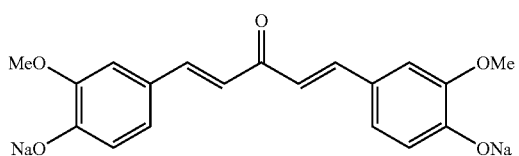

From the 1,5-bis(4-hydroxy-3-methoxy-phenyl)penta-1,4-dien-3-one in the presence of metallic alkoxide in a 1:2 molar ratio. Preferably, the 1,5-bis(4-hydroxy-3-methoxy-phenyl)penta-1,4-dien-3-one is mixed with an alcoholic solution of the respective alkoxide, followed by a rotoevaporation of the solvent until solid constitution. The disalt can be obtained with high yield. Once prepared, the phenolate is passed though a sieve in order to obtain a fine powder more easily solubilized in water and applied to the biological tests further described in this document.

The product shows a dark red colour.
General formula: $C_{19}H_{16}O_5Na_2$. Molecular weight: 370.
Yield: 95%.
Results from Structural Characterization:
UV-VIS: Maximum absorption is 370 nm in water.
Through hydrochloric acid acidification, the correspondent disalt is transformed into the correspondent 1,5-bis(4-hydroxy-3-methoxy-phenyl)penta-1,4-dien-3-one, which is extracted by ethyl ether or chloroform or ethyl acetate. The results of compound characterization are the same of the discussed above.

Example 3

Preparation of the 3,5-Bis-[3-methoxy-4-(3-methyl-but-2-enyloxy)-phenyl]-4-nitro-cyclohexanone (codified as C-25)

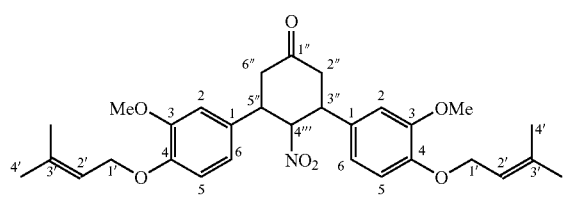 [SMILES: COc1cc(C2CC(=O)CC(c3ccc(OCC=C(C)C)c(OC)c3)C2[N+](=O)[O-])ccc1OCC=C(C)C]

Procedure for Preparation A

Previously, prepare a mixture containing from 5 to 20 mL of dimethylformamide, 1.38 g (0.01 mol) anhydrous potassium carbonate, and 0.01 mol (0.54 mL) of nitromethane, which should be heated under reflux at 20 to 70° C., stirring up for 30 to 60 minutes. After this period of time, add 0.001 mol (540 mg) of the compound 1,5-Bis[3-methoxy-4-(3-methyl-but-2-enyloxy)-phenyl]penta-1,4-dien-3-one dissolved in an appropriated quantity of dimethylformamide and let it heat under stirring for a period of 5 to 15 hours. After this time, the mixture are dropped into water and ice, acidified, extracted with ethyl acetate as required, and the organic phase washed with destined water. Dry with anhydrous sodium sulfate and rotoevaporate the solvent, obtaining the product of reaction.

Procedure for Preparation B

In this preparation procedure, an ultrasound technique is used, consisting of mixing 0.001 mol (540 mg) of 1,5-Bis[3-methoxy-4-(3-methyl-but-2-enyloxy)-phenyl]penta-1,4-dien-3-one with 5 to 20 mL of dimethylformamide and 0.01 mol (1.38 g) of anhydrous potassium carbonate, 0.01 mol (0.54 mL) of nitromethane, and let it react for a period of 3 to 10 hours at 30 to 70° C. At the end of the reaction, proceed as previously described in the preparation procedure 1.

The product is brownish colored.
General formula: $C_{30}H_{37}NO_7$. Molecular weight: 523.
Yield: 95%.

Results from the Quantitative Analysis:

| Calculation | | Found | |
|---|---|---|---|
| C | 68.83% | C | 68.79% |
| H | 7.07% | H | 7.10% |
| N | 2.68% | N | 2.65% |

Spectroscopic Analysis.

$^1$H-NMR (CDCl$_3$): Between 6.9 and 6.6 (m, 3H, H-2, H-5, H-6); 5.5 (m, 2H, H-2'); 5.2 (t, 1H, H-4"); 4.59 (d, 4H, H-1'); 3.80, and 3.88 (s, 6H, 2 MeO groups); between 3.0 and 2.8 (m, 6H, H-6", H-2", H-3", H-5"); 1.78 (s, 6H, Me), 1.73 (s, 6H, Me) ppm.

$^{13}$C-NMR (CDCl$_3$): 208.0 (CO); 149.0 (C-3); 148.0 (C-4); 138.0 (C-3'); 132.7 (C-1); 129.1 (C-6); 120.7 (C-2'); 113.1 (C-2); 111.2 (C-5); 92.2 (C-4"); 66.8 (C-1'); 56.1 (MeO); 43.0 (C-2", C-6"); 42.0 (C-3", C-5"); 26.0 (C-4'); 19.3 (C-4') ppm.

IV (film): 2970 ($C_{sp}{}^2$—H); 2933, 2916 ($C_{sp}{}^3$—H); 1712 (non-conjugate C=O), 1514 e 1381 (NO$_2$) cm$^{-1}$.

Example 4

Preparation of
3,5-Bis-(fur-2-yl)-4-nitro-1-cyclohexanone

Synthesis of substituted cyclic γ-nitroketones by Michael addition of nitroalkanes on divinylketones

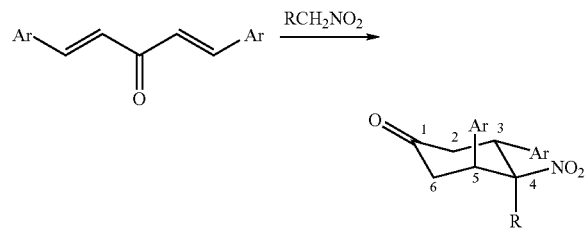

Procedure for Preparation A

Mix a pasty solution of the nitroalkane sodium salt, obtained by addition of 40 mmol of this product on 30 mmol (0.69 g) sodium solution in 5 to 20 mL of absolute MeOH, to a mixture of 20 mmol of the correspondent divinylketone in 20 to 40 mL of absolute MeOH. Stir the mixture up vigorously for a period of 4 to 8 hours, followed by external cooling with ice and stirring vigorously slowly, acidify with glacial acetic acid. Let the mixture in cold rest for a 5 to 12 hour period until product crystallization, which is filtrated and washed with MeOH. The residual water phases are extracted with diethylic ether, washed with water, and dried with anhydrous sodium sulfate. The ethereal extract is concentrated on a rotoevaporator and the resulting oil crystallizes from hot MeOH.

Procedure for Preparation B

Mix 1 mmol of divinylketone, 5 mmol of nitroalkane, and 1.4 mmol (0.2 g) of anhydrous potassium carbonate into 5 to 20 mL of EtOH. The mixture is refluxed for 5 to 10 hours. At reaction conclusion, add 20 to 40 mL of 5 water to the reagent mixture and extract with chloroform (3×10 mL). Chloroform extracts are washed with sufficient amount of destined water, dried with anhydrous sodium sulfate, and rotoevaporate the solvent until oil constitution. This oil is treated with hot EtOH and activated charcoal, producing solids that are separated by filtration at reduced pression.

Procedure for Preparation C

The reaction is performed in a similar manner to technique A, for this synthetic variant; however, it uses ultrasound irradiation between 30 and 70 kHz as the energy source, for a 1 to 4 hour interval. The products are isolated and purified as described in procedure A.

3RS-(3α,4β,5β)-3,5-di(fur-2-yl)-4-nitro-1-cyclohexanone

White crystals. Yield: Technique A: 60%; Technique B: 47%; Technique C: 75%,

Melting Temp. 92° C.

Molecular Formula: $C_{14}H_{13}NO_5$ (M=275.26)

| Elementary Analysis: | % C | % H | % N |
|---|---|---|---|
| Calculated | 61.09 | 4.76 | 5.09 |
| Observed | 61.29 | 4.60 | 5.14 |

EM: IE (70 eV), [M]$^+$=275 (12), 245 (11), 228 (76), 200 (53), 161 (40), 107 (100), 94 (41), 65 (30).

IR: (KBr) 1720 cm$^{-1}$ (CO), 1550, 1372.5 cm$^{-1}$ (NO$_2$).

$^1$H-NMR: (CDCl$_3$), δ (ppm): 7.34 (2H, m, H-5 Fur), 6.29 (2H, dd, H-4 Fur), 6.14 (2H, d, H-3 Fur), 5.44 (1H, dd, $J_{4-3a}$=13.23 Hz, $J_{4-5e}$=6.6 Hz, H-4), 4.07 (1H, dd, $J_{3a-4}$=13.2 Hz, $J_{3-2}$=6.6 Hz, H-3ax), 3.8 (1H, m, $J_{5-6e}$=3.9 Hz, $J_{5-4}$=5.53 Hz, $J_{5-6a}$=9.3 Hz, H-5ec), 3.05 (2H, m, H-2ax, H-6ax), 2.8 (2H, m, H-2ec, H-6ec).

$^{13}$C-NMR: (CDCl$_3$), δ (ppm): 204.61 (CO), 151.32, 150.48, 142.91, 142.75, 110.70, 110.55, 108.26, 108.12, (2 C-2, 2 C-5, 2 C-4, 2 C-3, C$_4$H$_3$O), 86.06 (C-4), 40.96, 40.89 (C-2, C-6), 37.30, 37.18 (C-3, C-5).

3RS-(3α,4β,5α)-3,5-di(fur-2-yl)-4-methyl-4-nitro-1-cyclohexanone

White scales Yield: Technique A: 28%; Technique C: 40%,

Melting Temp. 130-131° C. Molecular Formula: $C_{15}H_{15}NO_5$ (M=289.29).

| Elementary Analysis: | % C | % H | % N |
|---|---|---|---|
| Calculated | 62.28 | 5.23 | 4.84 |
| Observed | 62.20 | 4.93 | 4.82 |

EM: IE (70 eV), [M]$^+$=289 (2.5), 242 (80), 227 (50), 199 (30), 121 (100), 94 (80), 81 (75), 65 (48), 39 (63).

IR: (KBr) 1728 cm$^{-1}$ (CO), 1552, 1352 cm$^{-1}$ (NO$_2$).

$^1$H-NMR: (DMSO-d$_6$), δ (ppm): 7.6 (2H, m, $J_{5-4}$=1.8 Hz, H-5 Fur), 6.4 (2H, dd, $J_{4-3}$=3.2 Hz, $J_{4-5}$=1.87 Hz, H-4 Fur), 6.2 (2H, d, H-3 Fur), 4.35 (2H, C, $J_{3-2e}$=4.5 Hz, $J_{3-2a}$=14.17 Hz, H-3, H-5), 3.02 (2H, dd, $J_{2a-3}$=14.1 Hz, $J_{2a-2e}$=16.4 Hz, H-2ax, H-6ax), 2.6 (2H, m, $J_{2e-3}$=4.58 Hz, H-2ec, H-6ec), 1.4 (3H, s, Me).

$^{13}$C-NMR: (DMSO-d$_6$), δ (ppm): 203.73 (CO), 150.83, 143.10, 110.42, 108.27 (2 C-2, 2 C-5, 2 C-4, 2 C-3, C$_4$H$_3$O), 94.21 (C-4), 42.75 (C-3, C-5), 40.62 (C-2, C-6), 11.86 (Me).

3RS-(3α,4β,5α)]-3,5-diphenyl-4-methyl-4-nitro-1-cyclohexanone

White needles. Yield: Technique C: 85% (Lit. 40%).
Melting Temp. 187-188° C. (Lit. 188° C.) Molecular Formula: $C_{19}H_{19}NO_3$ (M=309.36).

| Elementary Analysis: | % C | % H | % N |
|---|---|---|---|
| Calculated | 73.77 | 6.19 | 4.53 |
| Observed | 73.64 | 6.10 | 4.64 |

EM: IE (70 eV), $[M]^+$=309 (1.5), $[M+1]^+$=310 (1), 280 (2), 260 (65), 247 (8), 219 (8), 205 (12), 175 (17), 159 (38), 131 (100), 104 (77), 91 (73), 77 (23).
IR: (KBr) 1725 cm$^{-1}$ (CO), 1538, 1341 cm$^{-1}$ ($NO_2$).
$^1$H-NMR: (CDCl$_3$), δ (ppm): 7.30-7.26 (6H, m, $C_6H_5$), 7.20-7.05 (4H, m, $C_6H_5$), 4.43 (1H, dd, H-5), 3.65 (1H, ddd, H-3), 2.95 (2H, dd, H-2ax, H-6ax), 2.7 (2H, dd, H-2ec, H-ec), 1.4 (3H, s, Me).
$^{13}$C-NMR: (CDCl$_3$), δ (ppm): 208.56 (CO), 137.68, 136.29 (2 C-1, $C_6H_5$), 129.10, 128.92, 128.81, 128.65, 128.56, 128.44, 128.35, 128.20, 128.11 (10CH, $C_6H_5$), 93.89, (C-4), 48.55, 46.45 (C-3, C-5), 42.16, 41.80 (C-2, C-6), 21.44 (Me).

Example 5

Preparation of 2,6-di-(arylalkyliden)-3,5-di-(fur-2-yl)-4-methyl-4-nitro-1-cyclohexanones One (1) mmol of the correspondent cyclohexanone A reacts with 4 mmol of the aldehyde in 5 mL of absolute MeOH and, under stirring and slowly conditions, a mixture of 4 mmol of sodium methanolate is dripped into 10 mL of absolute MeOH. Stirring is sustained for a 12 hour period. Solid precipitate is filtrated and the products isolated by chromatographic column and recrystallized.

3RS-(3α,4β,5α)]-2,6-di[1-(fur-2-yl)methyliden]-3,5-di(fur-2-yl)-4-methyl-4-nitro-1-cyclohexanone Yellow solid. R$_f$: 0.3 (n-heptan/ethyl acetate 3:1) Yield: 51%.
Melting Temp. 195-196° C. (MeOH-water) Molecular Formula: $C_{25}H_{19}NO_7$ (M=445.43)

| Elementary Analysis: | % C | % H | % N |
|---|---|---|---|
| Calculated | 67.41 | 4.30 | 3.14 |
| Observed | 67.26 | 4.03 | 3.11 |

EM: IE (70 eV), $[M]^+$=445 (3), 399 (29), 398 (80), 383 (24), 315 (18), 171 (18), 143 (23), 128 (70), 115 (100), 81 (52), 55 (45), 39 (55).
IR: (KBr) 1664 cm$^{-1}$ (CO), 1604 (C=C), 1536, 1344 cm$^{-1}$ ($NO_2$).
$^1$H-NMR: (DMSO-d$_6$), δ (ppm): 7.87 (2H, d, $J_{5-4}$=1.5 Hz, 2H-5 Fur in R$^1$), 7.71 (2H, s, H-7, H-8), 7.40 (2H, d, $J_{5-4}$=1.4 Hz, 2H-5 Fur em R), 6.88 (2H, d, $J_{4-3}$=3.4 Hz, 2H-3 Fur em R$^1$), 6.64 (2H, m, 2H-4 Fur em R), 6.14 (2H, m, $J_{4-3}$=3.25 Hz, 2H-4 Fur em R), 5.86 (2H, d, 2H-3 Fur em R), 5.60 (2H, s, H-3, H-5), 2.0 (3H, s, Me).
$^{13}$C-NMR: (CDCl$_3$), δ (ppm): 183.68 (CO), 150.45, 149.37 (2 C-2, $C_4H_3O$), 147.27, 142.06 (2 C-5, $C_4H_3O$), 127.27 (C-2, C-6), 126.50 (2 CH olef.), 119.63, 113.11 (2 C-3, $C_4H_3O$), 110.57, 109.80 (2 C-4, $C_4H_3O$), 92.87 (C-4), 48.55, 43.27 (C-3, C-5), 25.22 (Me).

3RS-(3α,4β,5α)]-3,5-diphenyl-2,6-di-[1-(fur-2-yl)methyliden]-4-methyl-4-nitro-1-cyclohexanone Yellow crystals. R$_f$: 0.34 (n-heptan/ethyl acetate 3:1), Yield: 60%
Melting Temp. 216-218° C. (DMF-water) Molecular Formula: $C_{29}H_{23}NO_5$ (M=465.51)

| Elementary Analysis: | % C | % H | % N |
|---|---|---|---|
| Calculated | 74.83 | 4.98 | 3.01 |
| Observed | 74.65 | 4.93 | 3.08 |

EM: IE (70 eV), $[M]^+$=465.1 (100), 419 (37), 418 (41), 403 (13), 335 (14), 208 (11), 194 (12), 165 (39), 153 (26), 105 (22), 81 (14), 77 (13).
IR: (KBr) 1665.8 cm$^{-1}$ (CO), 1600 (C=C), 1540, 1351 cm$^{-1}$ ($NO_2$).
$^1$H-NMR: (CDCl$_3$), δ (ppm): 7.91 (1H, s, H-7), 7.8 (1H, s, H-8), 7.58-7.47 (2H, d, H-5 Fur), 7.4-7.26 (10H, m, $C_6H_5$), 6.7-6.6 (2H, d, H-3 Fur), 6.5-6.4 (2H, dd, H-4 Fur), 5.6 (1H, s, H-3), 5.13 (1H, s, H-5), 1.67 (3H, s, Me).
$^{13}$C-NMR: (CDCl$_3$), δ (ppm): 189.19 (CO), 151.33, 151.17, 146.10, 145.82 (2 C-2, 2 C-5, $C_4H_3O$), 139.49, 137.82 (2 C-1, $C_6H_5$), 132.84, 130.37 (C-2, C-6), 130.18, 129.60, 128.77, 128.26, 127.76 (10 CH, $C_6H_5$), 127.04, 126.48 (2 CH olef.), 93.99 (C-4), 53.67, 48.33 (C-3, C-5), 25.21 (Me).

3RS-(3α,4β,5α)]-2,6-di-[1-(5-bromo-fur-2-yl)methyliden]-3,5-diphenyl-4-methyl-4-nitro-1-cyclohexanone Yellow solid. R$_f$: 0.3 (n-heptan/ethyl acetate 3:1) Yield: 65%
Melting Temp. 226-227° C. (MeOH-water) Molecular Formula: $C_{29}H_{21}Br_2NO_5$ (M=543.39)

| Elementary Analysis: | % C | % H | % N |
|---|---|---|---|
| Calculated | 64.10 | 4.90 | 3.58 |
| Observed | 63.87 | 4.76 | 3.57 |

IR: (KBr) 1668.3 cm$^{-1}$ (CO), 1611.4 (C=C), 1542, 1361 cm$^{-1}$ ($NO_2$).
$^1$H-NMR: (CDCl$_3$), δ (ppm): 7.6 (1H, s, H-8), 7.52 (1H, s, H-7), 7.25-7.1 (10H, m, $C_6H_5$), 6.42 (2H, m, H-3 Fur), 6.19 (2H, m, H-4 Fur), 5.26 (2H, s, H-3), 4.78 (1H, s, H-5), 1.5 (3H, s, Me).
$^{13}$C-NMR: (CDCl$_3$), δ (ppm) 187.12 (CO), 151.59, 151.54, 137.38, 136.04, 131.36, 130.04, 129.22, 128.81 (2 C-2, $C_4H_3O$, 2 C-1, $C_6H_5$, 2 C-5, $C_4H_3O$, C-2, C-6), 127.40, 127.35, 126.86, 126.53, 125.73, 125.57, 123.98, 123.78 (10 CH, $C_6H_5$, 2 CH olef.), 92.03 (C-4), 51.75, 47.99 (C-2, C-5), 23.54 (Me).

Example 6

Preparation of 2-(3,5-diaryl-4-nitrocyclohexyliden)malononitrile

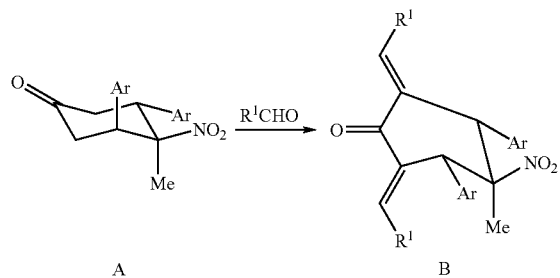

Ten (10) mmol of the correspondent 4-nitrocyclohexanone C reacts with 20 mmol of malononitrile, 12.9 mmol (1 g) of ammonium acetate, and 1 mL of glacial acetic acid in 60 mL of dry toluene. The mixture is put under reflux for 3 to 10 hours with the help of Dean-Stark. After this period, the reaction is cooled with aqueous solution of sodium carbonate (10%) and next with destined water. The organic fraction is dried with anhydrous sodium sulfate and concentrated by vacuum rotoevaporation, until oil constitution, which is crystallized from hot methanol.

3RS-(3α,4β,5β)]-[3,5-di(fur-2-yl)-4-nitrocyclohexyliden]malononitrile

Light green crystals.
Yield: 80%.
Melting Temp. 141-142° C. (MeOH) Molecular Formula: $C_{17}H_{13}N_3O_4$ (M=323.30)

| Elementary Analysis: | % C | % H | % N |
|---|---|---|---|
| Calculated | 63.16 | 4.06 | 13.00 |
| Observed | 63.15 | 4.12 | 12.95 |

EM: IE, (70 eV), $[M]^+$=323 (7), 293 (28), 276 (100), 247 (26), 209 (96), 173 (15), 115 (14), 94 (19), 83 (65).

IR: (KBr) 2232 cm$^{-1}$ (2 CN), 1600, 1500 (C=C), 1548, 1356 cm$^{-1}$ ($NO_2$).

$^1$H-NMR: ($CDCl_3$), δ (ppm): 7.40 (2H, dd, H-5 Fur), 6.38 (2H, m, H-4 Fur), 6.28 (1H, d, H-3 Fur), 6.20 (1H, d, H-3'Fur), 5.35 (1H, dd, $J_{4-3}$=12.8 Hz, $J_{4-5}$=5.8 Hz, H-4), 4.0 (1H, dd, $J_{3-2}$=11.1 Hz, $J_{3-2e}$=6.3 Hz, H-3ax), 3.8 (1H, m, $J_{5-6}$=3.1 Hz, H-5ec), 3.44 (2H, m, H-2ax, H-ax), 3.16 (2H, m, H-2e, H-6e).

$^{13}$C-NMR: ($CDCl_3$), δ (ppm): 175.71 (C=C), 150.09, 149.34, 143.4, 143.01, 110.94, 110.72, 108.74, 108.44 (2 C-2, 2 C-5, 2 C-3, 2 C-4, $C_4H_3O$), 111.12 (2 CN), 86.66 (=C(CN)$_2$), 85.93 (C-4), 37.17, 37.11 (C-3, C-5), 34.17, 33.96 (C-2, C-6).

3RS-(3α,4β,5β)]-[3,5-di(fur-2-yl)-4-methyl-4-nitrocyclohexyliden]malononitrile Light gray crystals.
Yield: 85%,
Melting Temp. 192° C. (MeOH)
Molecular Formula: $C_{18}H_{15}N_3O_4$ M=337.33).

| Elementary Analysis: | % C | % H | % N |
|---|---|---|---|
| Calculated | 64.09 | 4.48 | 12.46 |
| Observed | 64.36 | 4.43 | 12.24 |

EM: IE (70 eV), $[M-47]^+$=290 (20), $[M-46]^+$=291 (60), 275 (100), 222 (20), 147 (18), 128 (20), 115 (27), 95 (52), 81 (98), 65 (41), 53 (54), 39 (88).

IR: (KBr) 2240 cm$^{-1}$ (2 CN), 1608, 1504 (C=C), 1548, 1352 cm$^{-1}$ ($NO_2$).

$^1$H-NMR: ($CDCl_3$), δ (ppm): 7.62 (2H, d, H-5 Fur), 6.44 (2H, dd, H-4 Fur), 6.32 (2H, d, H-3 Fur), 4.18 (2H, dd, $J_{3-e}$=5.0 Hz, $J_{3-a}$=14.4 Hz, H-3ax, H-5ax), 3.28 (2H, m, $J_{a-3}$=14.2 Hz, H-2ax, H-6ax), 3.10 (2H, m, $J_{e-3}$=5.1 Hz, H-2ec, H-6ec), 1.3 (3H, s, Me).

$^{13}$C-NMR: ($CDCl_3$), δ (ppm): 177.35 (C=C), 150.17, 143.32, 110.49, 108.59 (2 C-2, 2 C-5, 2 C-4, 2 C-3, $C_4H_3O$), 111.73 (2 CN), 93.91 (C-4), 84.01 (=C(CN)$_2$), 43.12 (C-3, C-5), 33.38 (C-2, C-6), 11.93 (Me).

Part 2

Antitumoral Activity and Pertinent Pre-Clinical Assays

The present invention also refers to the in vivo antitumoral activity for the above mentioned derivatives as well as to their precursor 1,5-bis(4-hydroxy-3-methoxy-phenyl)penta-1,4-dien-3-one.

It also refers to the in vivo antitumoral activity of an association prepared from 1,5-bis(4-hydroxy-3-methoxy-phenyl)penta-1,4-dien-3-one (HB-1) and 4-[5-(4-acetoxy-3-methoxy-phenyl)-3-oxo-penta-1,4-dienyl]-2-methoxy-phenylacetate (HB-2) in an appropriate molar ratio and in an adequate solvent.

The compounds herein present have shown significant antiproliferative activity, comprising cytostatic and cytotoxic actions in tests performed in vivo, in addition to be shown as almost atoxic, the latter characteristic being quite advantageous.

The observed activities are illustrated through the following examples:

Example 7

Figure 1:
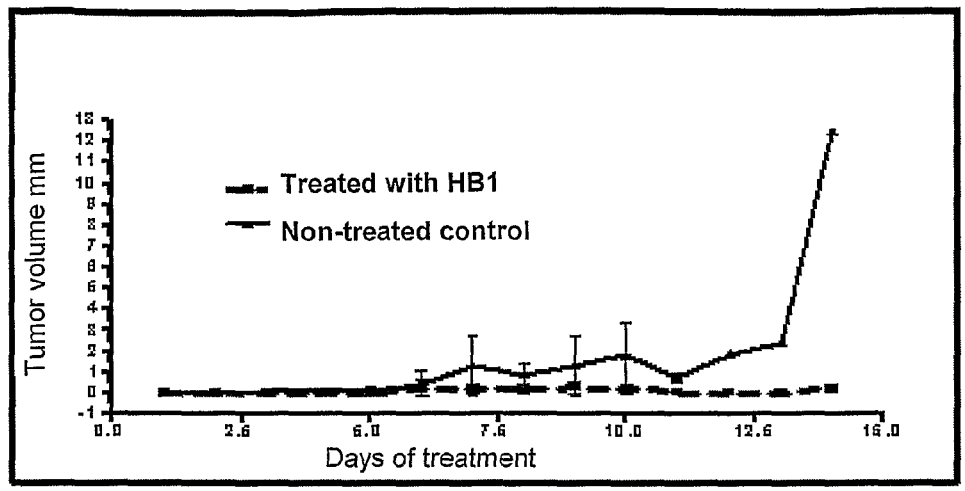
FIG. 1—Evaluation of B16F10 murine melanoma growth (volume) after treatment with HB-1.
Figure 2:
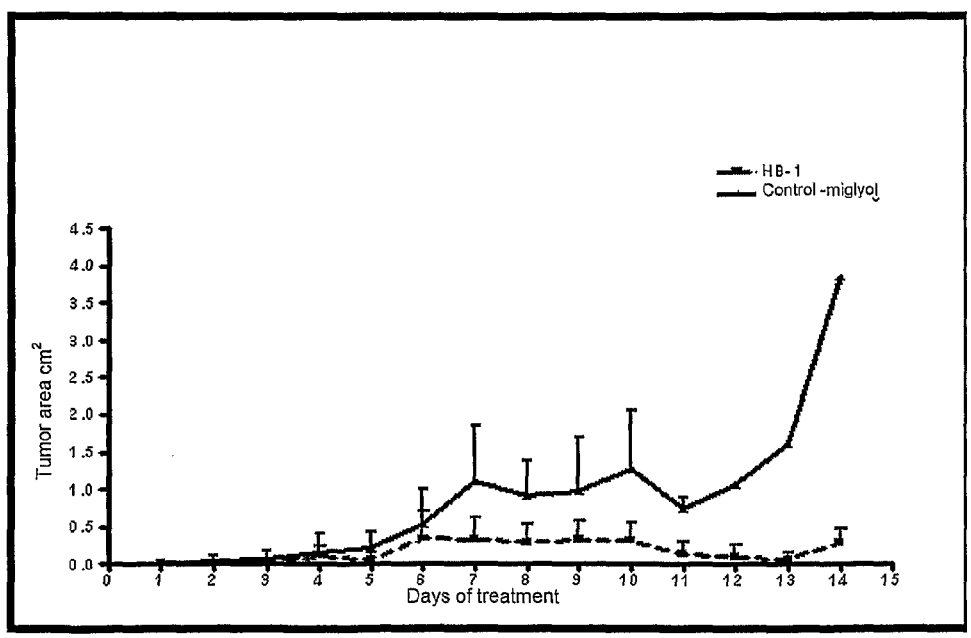
FIG. 2—Evaluation of B16F10 murine melanoma growth (area) after treatment with HB-1.

Analysis of the Inhibitory Capacity (Volume and Tumoral Area for the HB-1 Compound in Melanoma Tumors Implanted in C57BL/6J Mice, Treated by the Intraperitoneal. (1.15 μg/kg Daily) Route. FIGS. 1 and 2 Illustrate this Analysis After the Day 4 of tumor cells implant ($2 \times 10^5$ tumoral cells/mL), the animals were splitted in two groups: the test group, treated with HB-1 compound diluted in Miglyol 810® and the control group, which received only the diluent (Miglyol 810®) in the same volume as the test group. The animals were daily treated by intraperitoneal route. Concomitantly, measurements of animal weight and tumor size (two measures—length×width) were performed and tumor aspect registered by photographies.

After the Day 14, the animals were sacrificed by cervical displacement, tumors were removed, and necropsy performed to remove all internal organs and macroscopic lesions for hystopathologic analysis.

Tumoral parameters were obtained by calculation of tumor average area (A) and volume (V), through the following formulas $A=\pi R^2$ and $V=4/3\pi R^3$, where (R=average tumor radius).

Our results have shown high significance to reduce tumoral parameters (volume and area), after the treatment with the HB-1 compound diluted in Miglyol 810®. During treatment, we have observed that the animals that received the HB-1 compound diluted in Miglyol 810® have not shown, at any point, exponential growth of dorsal tumor, which have occurred in the control group that received only Miglyol 810®. The percentage of inhibitory treatment for B16F10 melanoma was higher than 98%, clearly showing its efficacy to reduce and inhibit tumoral proliferation.

Example 8

Macroscopic Aspect

Control Group—Macroscopic Aspect of Dorsal Tumor→Melanoma.

Figure 3:
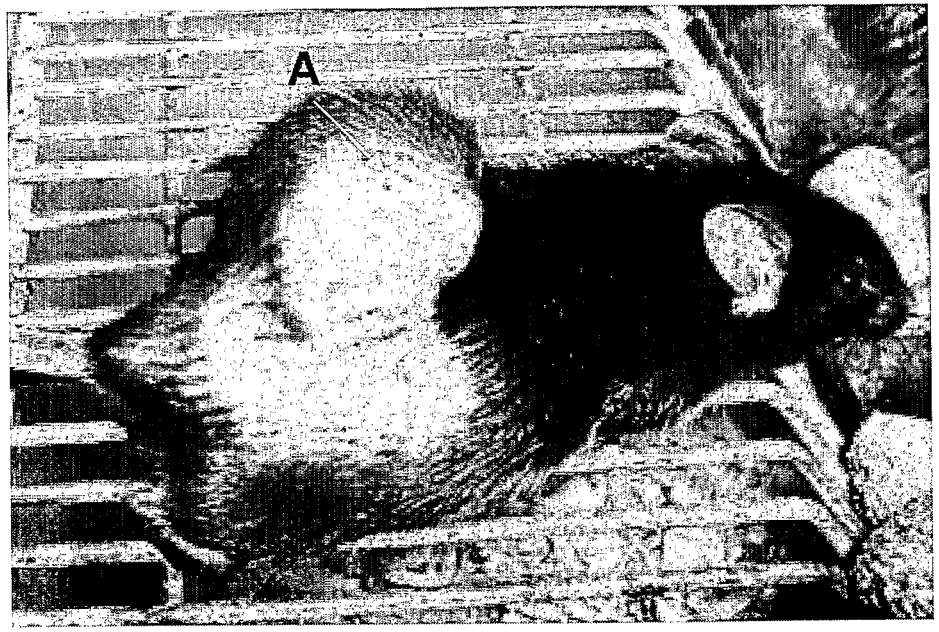
FIG. 3—Control group: Miglyol 810®.
A—Pigmented and nodular dorsal tumor.
Figure 4:
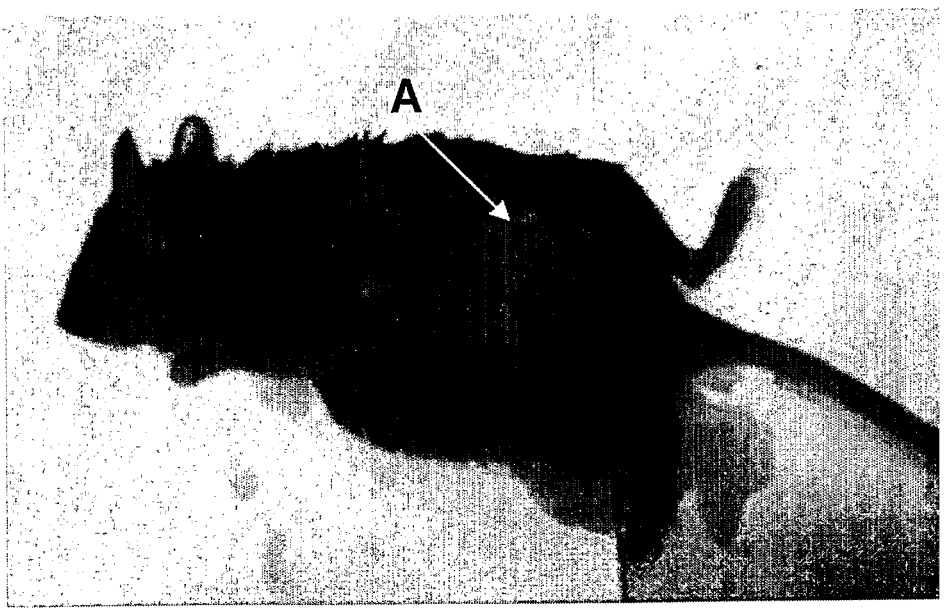
FIG. 4—Control group: Miglyol 810®.
A—Pigmented and nodular dorsal tumor.
Figure 5:
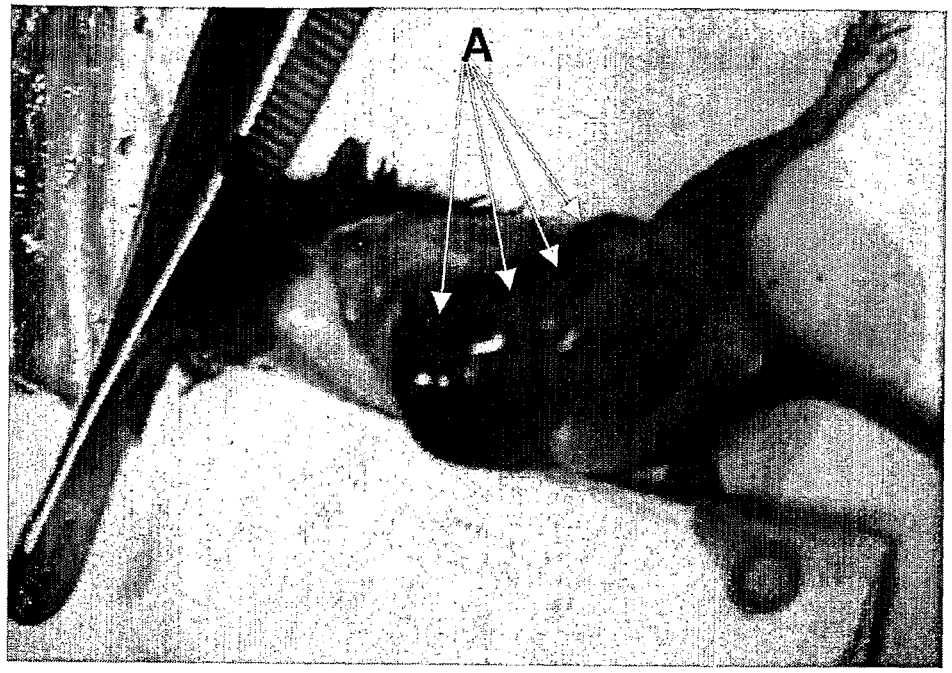
FIG. 5—Control group: Miglyol 810®.
A—Dorsal tumor. A great area of peripheral irrigation is observed.

The pigmented dorsal tumor of nodular aspect in the control group, occupying ¾ of the animal body volume is shown in the FIGS. 3 and 4. FIG. 5 shows, for the same group, the macroscopic aspect after tumor necropsy. In this Figure we can observe the peripheral irrigation system (angiogenesis) of the dorsal tumor (melanoma).

Treated Group—Macroscopic Aspect of Dorsal Tumor→Melanoma.

Figure 6:
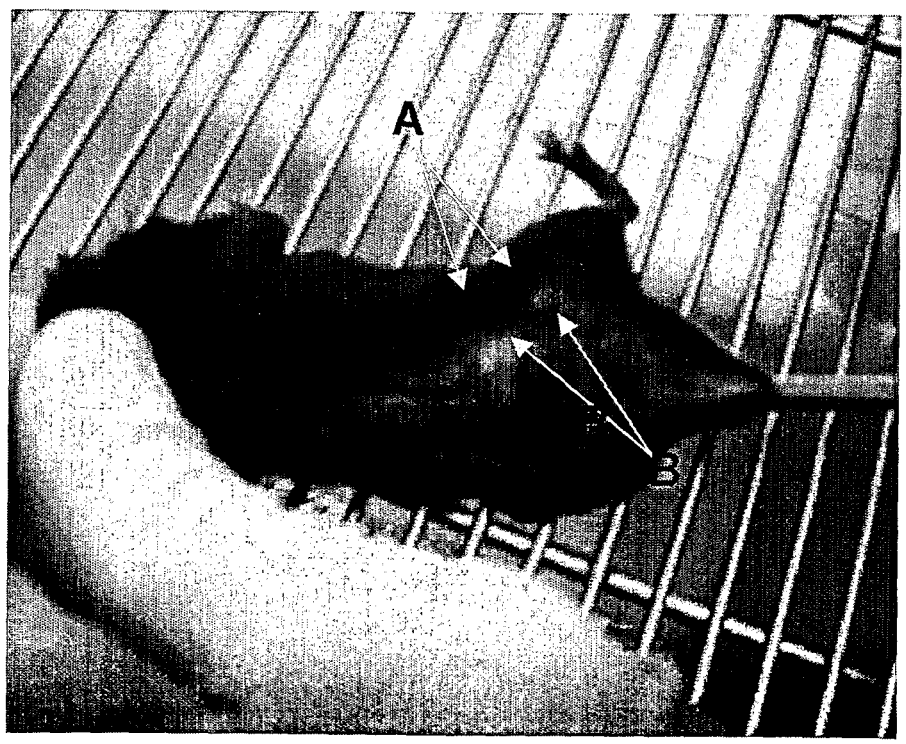
FIG. 6—Dorsal tumor in the treated group. HB-1 compound in Miglyol810®.
A—Dorsal tumor for the HB-1 compound.
B—Necrosis.
Figure 7:
FIG. 7—Dorsal tumor in the treated group. HB-1 compound in Miglyol810®.

The pigmented dorsal tumor resulting from the treated group is shown in FIGS. 6 and 7. We can observe a small pigmented dorsal tumor, lack of nodules or ulcerations. Necrosis areas may be observed as lacking tumoral growth.

Figure 8:
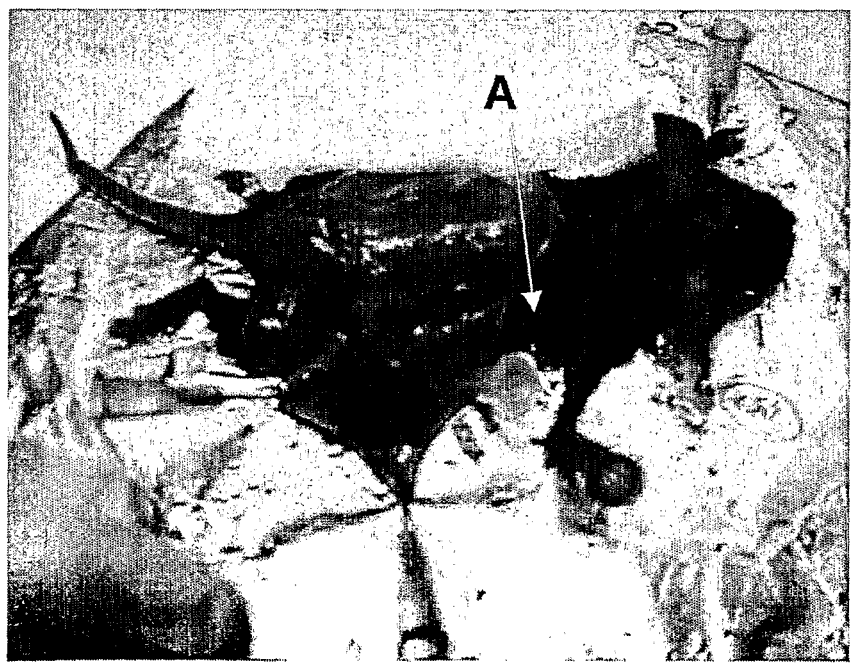
FIG. 8—Dorsal tumor in the treated group. HB-1 compound in Miglyol810®.
A—Dorsal tumor. Peritumoral exsudate is observed.
Figure 9:
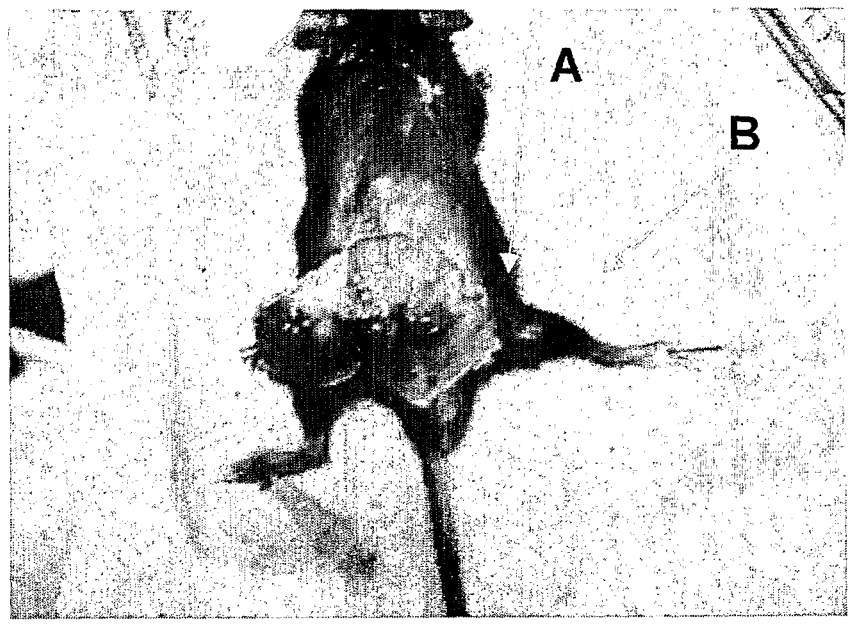
FIG. 9—Dorsal tumor in the treated group. HB-1 compound in Miglyol810. A great area of peripheral irrigation is observed.
A—Peritumoral exsudate.
B—Vascular system+necrosis.

The macroscopic aspect of the vascular system and peritumoral exsudate of the dorsal tumor (melanoma) in the treated group is shown in FIGS. 8 and 9. A reduction of the tumor irrigation system and the development of cellular and/or serous infiltrate around the tumor may be observed.

Determination of Cell Cycle Phases Through Flow Cytometry of Melanoma Dorsal Tumors Treated for 14 Days with the HB-1 Compound by the Intraperitoneal Route.

Figure 10:
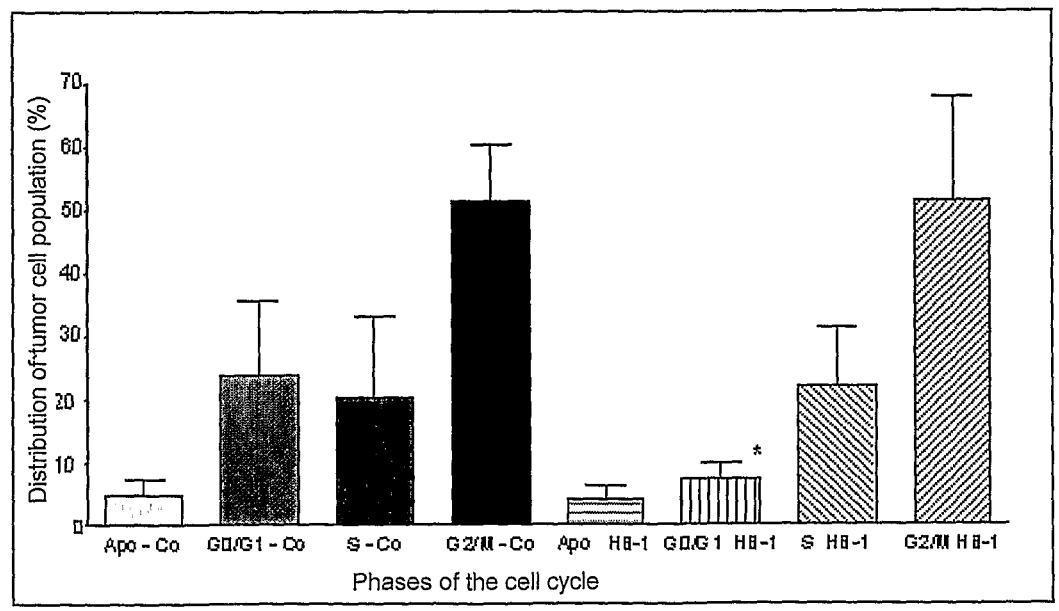
FIG. 10—Analysis of the phases of cell cycle of B16F10 melanoma treated with 15 mg/kg HB-1.

The analysis of the cell cycle of B16F10 melanoma treated with 15 mg/kg HB-1 is shown in FIG. 10. Aliquots of the tumoral cells suspensions ($10^6$ cells/mL) for the control group that received Miglyol 810® vehicle and of the animals treated with the HB-1 compound for 14 days by the intraperitoneal route were immediately frozen in citrate (2 mM), sucrose (25 mM), and 0.05% dimethyl sulfoxide (DMSO) buffer, kept in liquid nitrogen up to the moment of use. After sample thawing in an ice bath, the cells were incubated with 375 µL of 0.03 g/L trypsin (Sigma) for 10 minutes, at room temperature, and neutralized with 0.5 g/L trypsin inhibitor (Sigma), 0.1 g/L ribonuclease A (Sigma), and 1.2 g/L spermine (Sigma). The samples were analysed by a flow cytometer (Becton-Dickson) and the percentage of cells was evaluated for the different phases of the cell cycle, apoptosis level (Sub-G1), and DNA content in phase S, quiescent cells (G0/G1), and cells in premytosis (G2/M).

Figure 11:
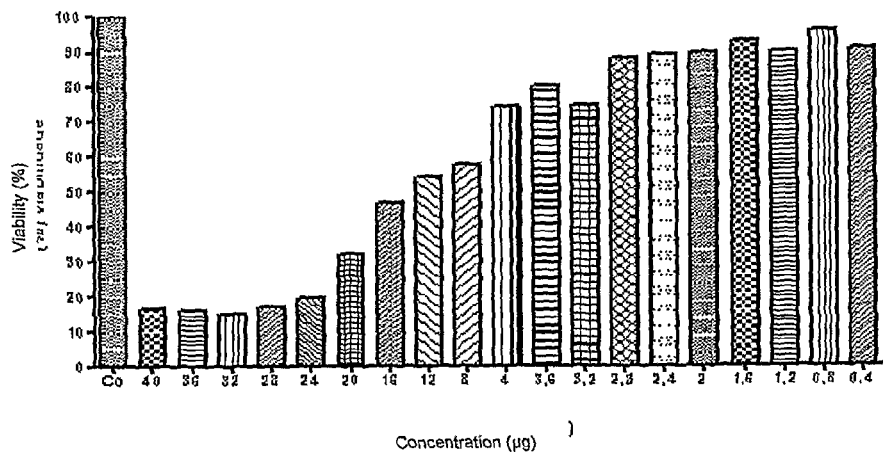
FIG. 11—Toxicity assay (HB-1) in B16F10 murine melanoma cells.

Our results (FIG. 11) have shown that HB-1 compound diluted in Miglyol 810® significantly reduces the tumoral cell population in the G0/G1 phase of the cell cycle. This result demonstrates that HB-1 compound is able to hinder tumoral cell multiplication, with the same qualities as the chemotherapic drugs of routine use for human malignant neoplasia treatment, such as doxorubicin, sodium methotrexate, or last generation drugs derivated from paclitaxel and etoposide.

Analysis of Cytotoxic and Antiproliferative Effects of HB-1 Compound and Miglyol 810® as Control by the MTT Colorimetric Method on B16F10 Melanoma Cells.

Figure 12:
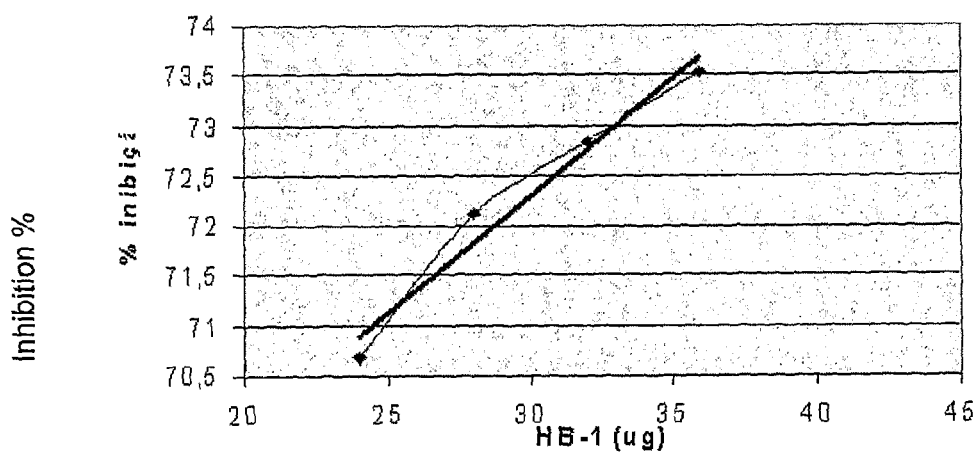
FIG. 12—Cytotoxic antiproliferative effect of HB-1 compound diluted in Miglyol 810 for B16F10 murine melanoma cells.

The cytotoxic and antiproliferative effects of cellular strains and normal cells were performed in different concentrations of HB-1 compound diluted in Miglyol 810®, and, as control, the diluent used for all dilutions performed and also commercial chemotherapics (Paclitaxel, Etoposide). The colorimetric methodology for the respiratory route of mitochondria MTT (3-(4,5-dimethylthiazol-2-yl)2,5-diphenyl tetrazolium bromide) was used, as described by MOSMANN (1983). This method is based on the reduction of MTT to formazan by living cells. After growth and in vitro confluence of normal and tumoral cells, different concentrations of the HB-1 compound diluted in Miglyol 810® and the diluent-control (Miglyol 810®) have been added on the adhering cells, incubated for 24 hour. After the referred period, 10 µl of MTT (5 mg/mL) were added and incubated for 3 hours in stove with 5% $CO_2$ at 37° C. After this period, the content of the culture plates were centrifuged for 2 minutes at 1800 rpm, at 4° C., the supernatant was removed and 100 µL of dimethyl sulfoxide (DMSO) were added to dissolve formazan crystals previously constituted and precipitated. The absorbances were obtained by an ELISA reader at 540 nm (TiterTek Multiskan) wavelength, with the results obtained shown in FIG. 12.

$IC_{50}$ Evaluation for B16F10 Melanoma Cells, Obtained from the Linear Equation.

$IC_{50}=7.0$ µg/mL of HB-1 compound diluted in Miglyol 810®.

Cytotoxic Effect of HB-1 Compound on Peritoneal Normal Macrophages Assessed by the MTT Method.

Peritoneal macrophages were obtained from normal Balb-C mice through the following procedure: abdominal cavities of the animals were opened under sterile conditions under a laminar flow and exposed. A 2 mL volume of saline solution, containing 5000 U frosty heparin (Liquemine-Roche), was injected into the cavity, followed by a massage and collection of the peritoneal wash irrigation liquid, centrifuged at 2000 rpm for 10 minutes at 4° C.

Figure 13:
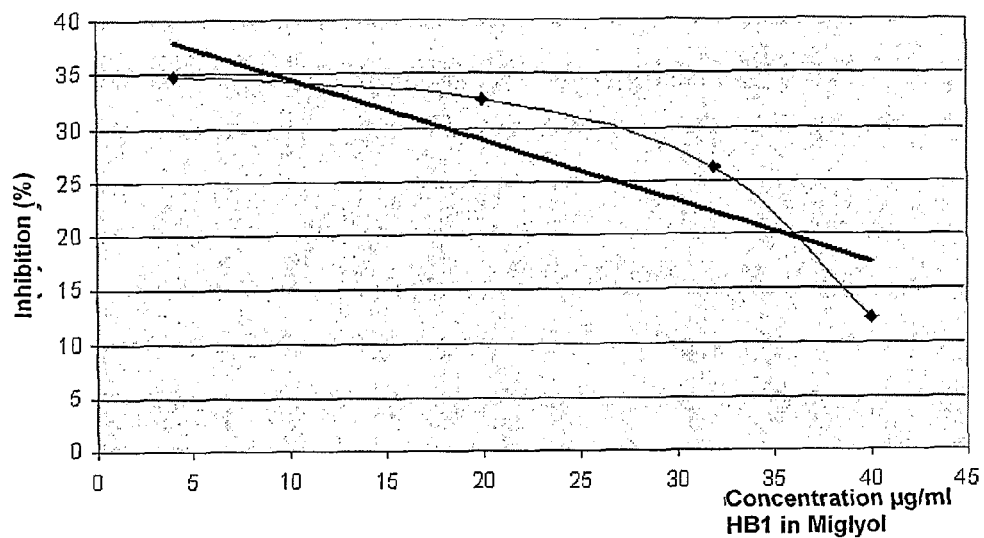
FIG. 13—Cytotoxic antiproliferative effect of HB-1 compound diluted in Miglyol 810 on peritoneal normal macrophages.

The suspension was resuspended with RPMI-1640 culture medium supplemented with 10% bovine fetal serum, with the count cell number adjusted to $10^6$/mL in a Neubauer chamber. Aliquots of the macrophages were cultivated on plates with 96 flat bottom wells, incubated with and without HB-1 compound diluted in Miglyol 810®. After 24 hours, the plates were submitted to the cytotoxic and antiproliferative effect assessment by the MTT calorimetric method. The results obtained are shown in FIG. 13.

$IC_{50}=16.89$ µg/mL for the HB-1 compound diluted in Miglyol 810®.

Toxic Effects Evaluation by Cachexia (Total Body Weight Loss) Index for the In Vivo Treatment, for 14 Days, by Intraperitoneal Route For Animals Bearing Dorsal Melanomas and Treated with HB-2 and (HB-1+HB-2) Conjugate Compounds.

Animals of the control group bearing a melanoma dorsal tumor received, by the same route, an equal volume of diluent (100 µl Miglyol 810®).

Figure 14:
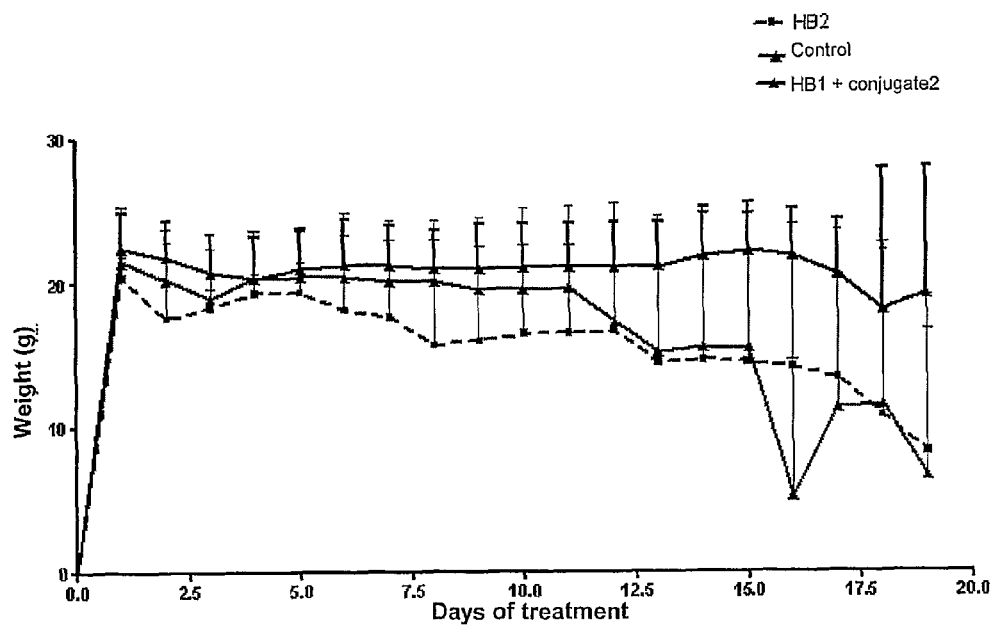
FIG. 14—Assessment of cachexia index for animals bearing tumor B16F10 melanoma.

Before receiving HB-2 and HB-1+HB2 conjugate, the animals were daily weighted and apparently have not shown macroscopic (hair loss—alopecia) or behavioral (mobility, irritability or euphoria) modifications. Our results (FIG. 14) showed that the animals treated with the HB-2 compound diluted in Miglyol 810® and the control group presented similar behavior as for weight loss, which was expected for the animals bearing tumors. On the other hand, the groups of animals that received the (HB2+HB-1) conjugate have not shown significant weight loss modifications throughout the treatment and no weight loss was observed when compared to HB-2 and control groups. Our results have shown that the conjugate, in spite of not being efficient to control the tumor volume or area, shows in vivo low toxicity.

Analysis of In Vivo Antitumoral Parameters (Volume) to Treat B16F10 Melanoma with HB-2 Compound and (HB-1+HB-2) Conjugate.

Figure 15:
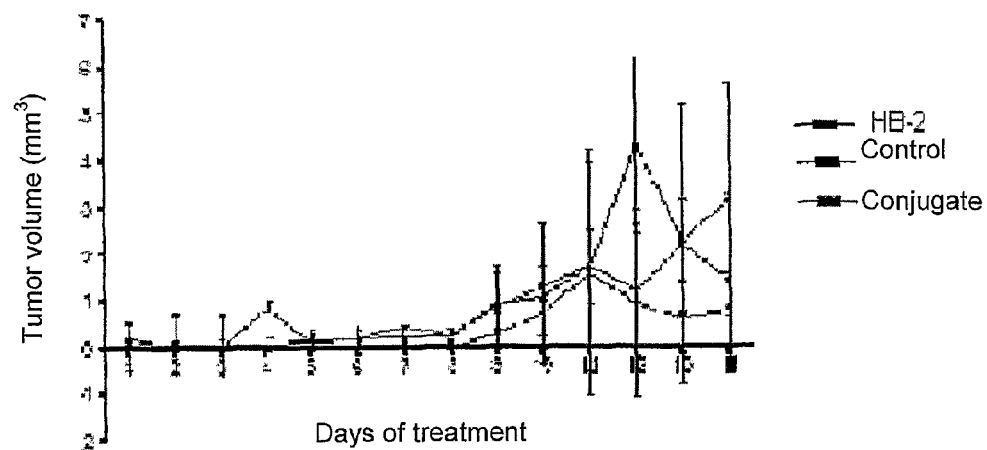
FIG. 15—Assessment of HB-2 compound, HB-1+HB2 (association), and Miglyol (control) in implanted melanoma B16F10 in to C57BL/6J mice.

The analysis of in vivo antitumoral parameter (volume) to treat B16F10 melanoma with HB-2 compound and (HB-1+HB-2) conjugate is shown in FIG. 15.

Analysis of In Vivo Antitumoral Parameters (Area and Volume) to Treat B16F10 Melanoma with HB-2 Compound and (HB-1+HB-2) Conjugate.

After tumoral cell implant, the animals were treated with the HB-2 compound diluted in Miglyol 810® and with (HB2+HB-1) conjugate whereas the control group received the same volume of diluent and by the same administration route (intraperitoneal—100 μl). Daily, the animals received the compounds (100 μl) and the control group received Miglyol 810®, the animals were weighted, and the tumors were measured (length×width) and photographed. After Day 14, the animals were sacrificed by cervical displacement, the tumors were removed to perform necropsis and the internal organs and macroscopic lesions removed for histopathologic analyses.

Figure 16:
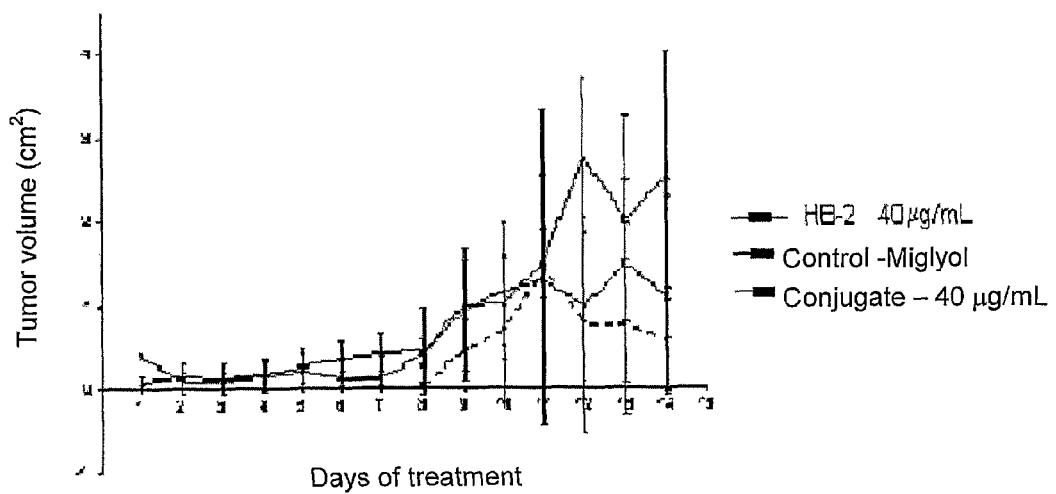
FIG. 16—Assessment of HB-2 compound and HB1+HB2 (association) in implanted melanoma B16F10 in to C57BL/6J mice-Area.

Tumoral parameters were obtained by calculation of tumor average area (A) and volume (V), through the following formulas $A=\pi R^2$ and $V=4/3\pi R^3$. Results are shown in FIG. 16.

In relation to the antitumoral effects from B16F10 dorsal melanoma treatment, HB-2 compounds and (HB-2+HB-1) association have showed to be important antiproliferative agents, significantly reducing the tumoral burden in 60% for the HB-2 compound and 80% for (HB-1+HB-2) association, respectively, for both tumor area and volume.

Analysis of Cytotoxic and Antiproliferative Effects from HB-2 Compound Diluted in Miglyol 8100 and Miglyol 810® Control by the MTT Colorimetric Method on the B16F10 Melanona Cells.

$IC_{50}$=90.28 μg/mL of HB-2 compound diluted in Miglyol 810®.

Figure 17:
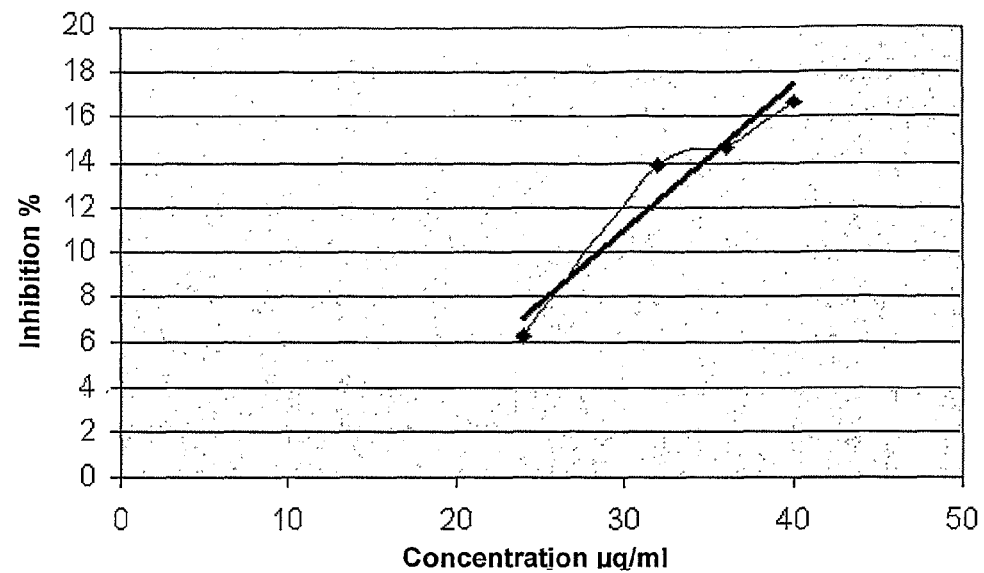
FIG. 17—Cytotoxic antiproliferative effect for HB-1 compound diluted in Miglyol on B16F10 melanoma cells.

In vitro treatment of B16F10 melanoma with HB-2 compound diluted in Miglyol 810® have presented, as shown in FIG. 17, low cytotoxic effect in relation to the other compounds, a $IC_{50}$ of approximately 90.3 μg/mL obtained by the linear equation. This compound has shown low in vitro toxicity; however, when conjugated with HB-1 compound, it has shown in vivo antitumoral therapeutic efficacy with an 80% reduction of tumor area and volume.

Analysis of Cytotoxic Effects by the MTT Method and Antiproliferative Effects for HB-2 Compound Diluted in Miglyol 810® and Miglyol 810® Control on Human Fibroblasts of Normal Skin.

Skin fragments were asseptically collected during surgical procedures for tissue remotion in aesthetic surgery and immediately transferred to 50 mL sterile vials containing HAM F-12 (Gibco) culture medium supplemented with 20% of bovine fetal serum. Fragments were chopped, cleaned, and the smaller fragments were cultivated in Petri dishes in a Ham-F12 culture medium supplemented with 10% bovine fetal serum, and kept in humidified stoven at 37° C. and 5% $CO_2$.

When attained subconfluence, the cells were trypsinized for 5 minutes, inactivated with 10% bovine fetal serum, centrifuged for 10 minutes at 2000 rpm at 4° C., transferred to 96 well flat bottom plates, and cultivated for 24 hours in a $CO_2$ 5% stoven. Fibroblasts were treated for 24 hours with different concentrations of HB-2 compound diluted in Miglyol 810® and the control group received the same volumes of Miglyol alone; cytotoxic and antiproliferative effects were evaluated by the MTT colorimetric method.

Figure 18:
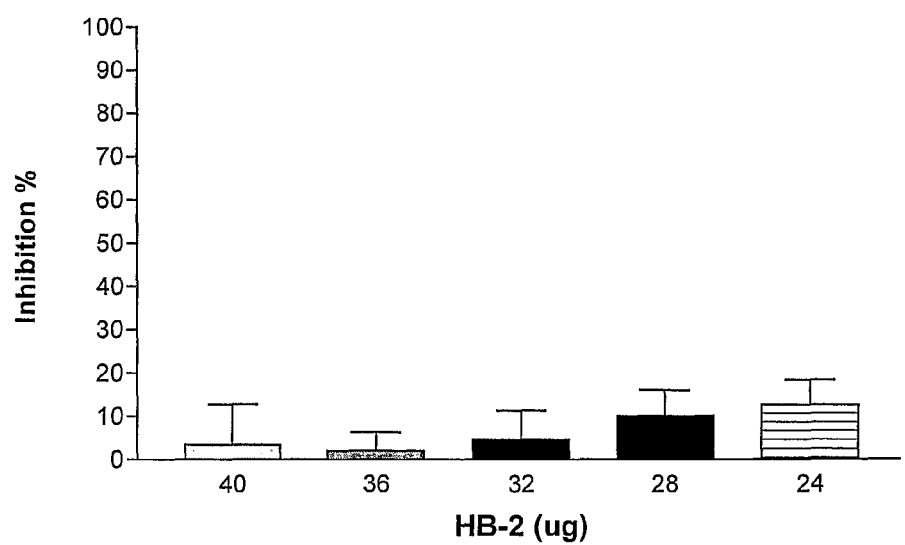
FIG. 18—Assessment by the MTT method of the antiproliferative and cytotoxic effect of HB-2 compound diluted in Miglyol 810® and Miglyol 810® control on normal skin human fibroblasts.

As shown in FIG. 18, no cytotoxic effect was observed in normal human fibroblasts after treatment with HB-2 compound diluted in Miglyol 810®.

Analysis of Cytotoxic Effects by the MTT Method and Antiproliferative Effects of Monosodium HB-1 Compound and Control on B16F10 Murine Melanoma.

$IC_{50}$=1.9 μg/mL of the DM-1 compound.

Figure 19:
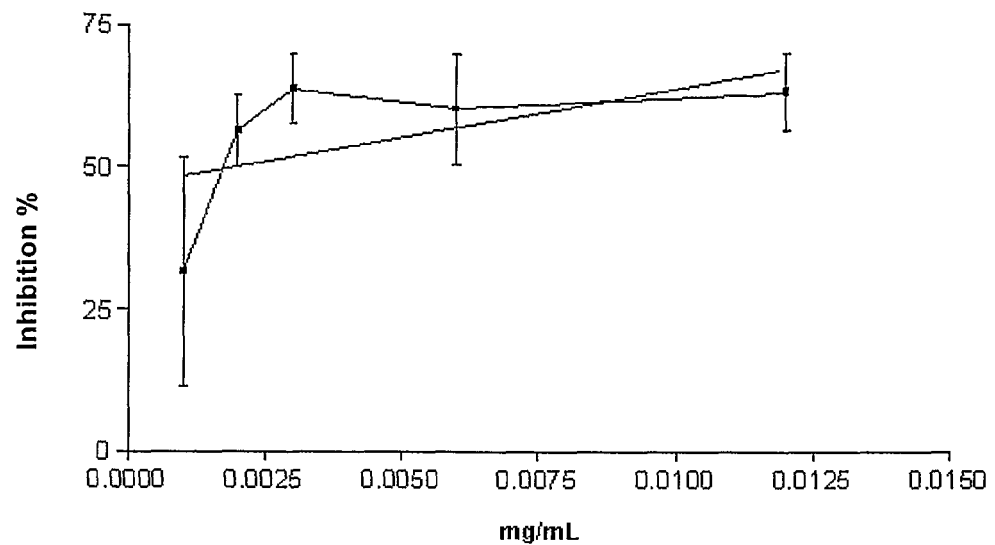
FIG. 19—Assessment of antiproliferative and cytotoxic effects of monosodium compound on B16F10 melanoma cells.

Our results (FIG. 19) have shown that the monosodium drug composition of HB-1 compound has significantly increased the cytotoxic response on B16F10 melanoma cells, exhibiting $CI_{50\%}$=1.9 μg/mL. Its in vitro efficacy has a 7.0 fold increase in cytotoxic effects.

Analysis of Cytotoxic Effects by the MTT Method and Antiproliferative Effects of DM-2 Compound and Control on B16F10 Murine Melanoma Cells.

$IC_{50}$=7.95 μg/mL of the DM-2 compound.

Figure 20:
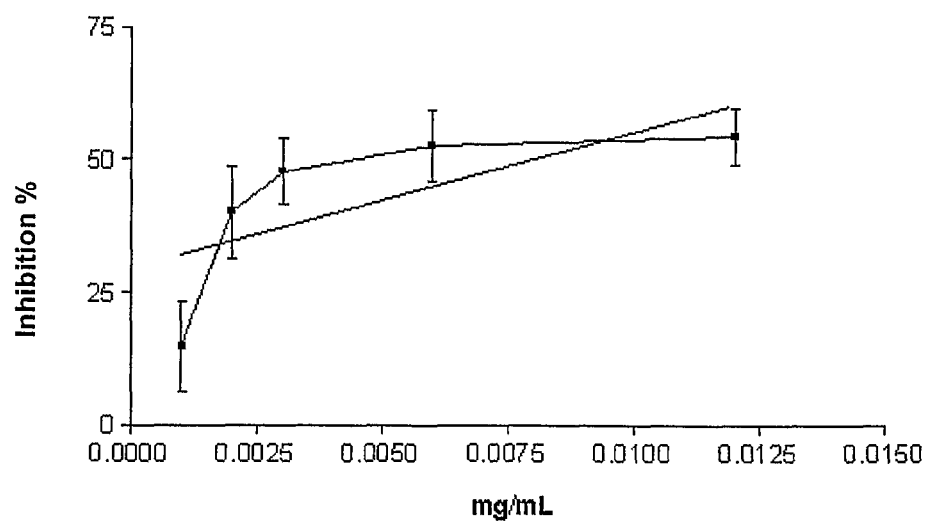
FIG. 20—Assessment of antiproliferative and cytotoxic effects of disodium compound on B16F10 melanoma cells.

Our results (FIG. 20) have shown that drug composition for the DM-2 compound has significantly increased the cytotoxic response in B16F10 melanoma cells, exhibiting $IC_{50}$=7.95 μg/mL. In vitro, the efficacy in relation to the monosodium DM-1 compound is around 6.0 fold smaller.

Therefore, the monosodium derivative is superior to the disodium derivative.

$IC_{50}\%$=7.95 μg/mL of the DM-1 compound.

Assessment of DM-2 Compound on T Lymphocytes.

Example 9

Preparation of T Lymphocytes

Groups composed by 5 C57BL/6J mice of 2 months of age were sacrificed by cervical displacement and its lymph nodes chain from axillary, popliteal, and mesenteric regions were removed under sterile conditions. Lymph nodes were maintained in RPMI-1640 culture medium supplemented with 10% inactivated bovine fetal serum at 56° C. in the presence of antibiotics, and debridement was performed with the assistance of a bistury. The resulting cell suspension was filtered through 30 μm dialysis membrane and centrifuged for 10 minutes at 1800 rpm at 4° C. Cell pellet was resuspended in 5 mL RPMI complete medium and, after that, incubated in Petri dishes containing 10 mL bovine fetal serum for 1 hour in stove, at 37° C. and 5% $CO_2$. After this period, the non-adhering cells, T lymphocytes, were collected and transferred to 50 mL conic tubes, centrifuged and resuspended in RPMI-1640 complete medium. Cell concentration was adjusted in Mallassez chamber to a 5×10^5 cells/mL concentration and cell viability was determined by the exclusion method with Trypan blue.

Cytotoxic and proliferative activities were determined in a 96 well plate and compared to mitogenic activity of phytohemagglutinin (PHA) and evaluated by the MTT calorimetric method. The obtained values were expressed as percentage.

The data of each experiment were statistically analysed by the ANOVA variance test with de p<0.05 significance.

Figure 21:
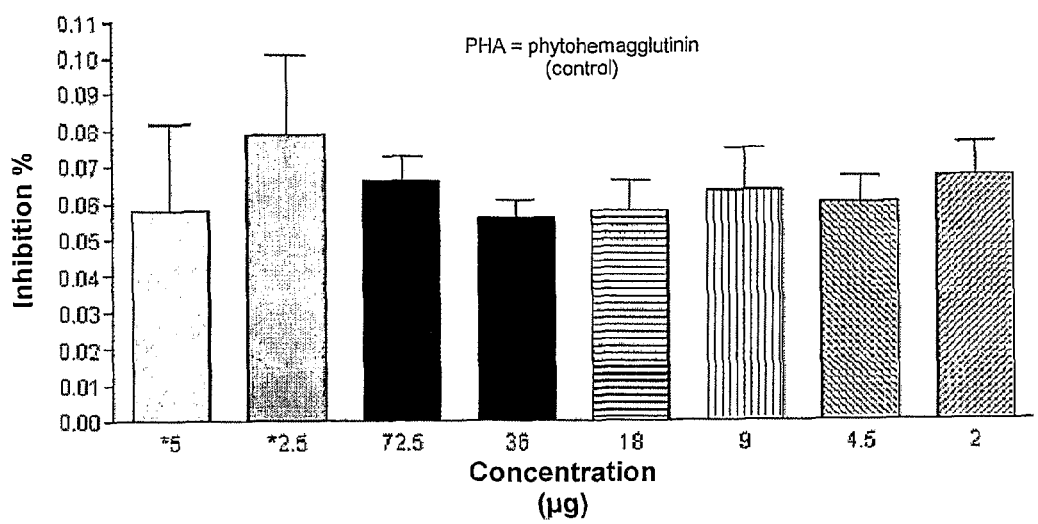
FIG. 21—Assessment of antiproliferative and cytotoxic effects of DM-2 compound on T lymphocyte.

Our results (FIG. 21) have shown that the treatment of lymphocytes with different concentrations of the DM-2 compound have induced no proliferative activity of these cells when compared to those of phytohemagglutinin (PHA) at optimal concentrations of 2.5 and 5.0 μg, as positive control. These results have shown that the compound presents no toxic activity on normal cells and it is unable to induce a proliferative activity as a specific immune response, which would be responsible for adverse reactions such as immune complexes production, allergic, and hypersensitive or self-immune reactions.

Acute and Subchronic Toxicology of DM-1 in Balb-c Mice by the Endovenous Route.

$LD_{50}$=14 mg/Kg/animal~700 mg/body weight.

Balb-c mice were weighted and housed in the biotery, subdivided into groups of 05 animals per cage and, after two weeks, received the DM-1 compound in different concentrations by the endovenous route. The compound was administered in a 0.2 mL volume using microseringe, for all concentrations, through the retro-orbital venous plexus. After the administration, no behavioral alteration was observed, such as decrease of motility, exhaustion, impaired breath frequency, or endovolemic shock.

After 24 hours, mortality and total body weight loss from treated animals was observed in order to determine the maximum tolerable dose (MTD); this group of animals was observed for 60 days.

Figure 22:
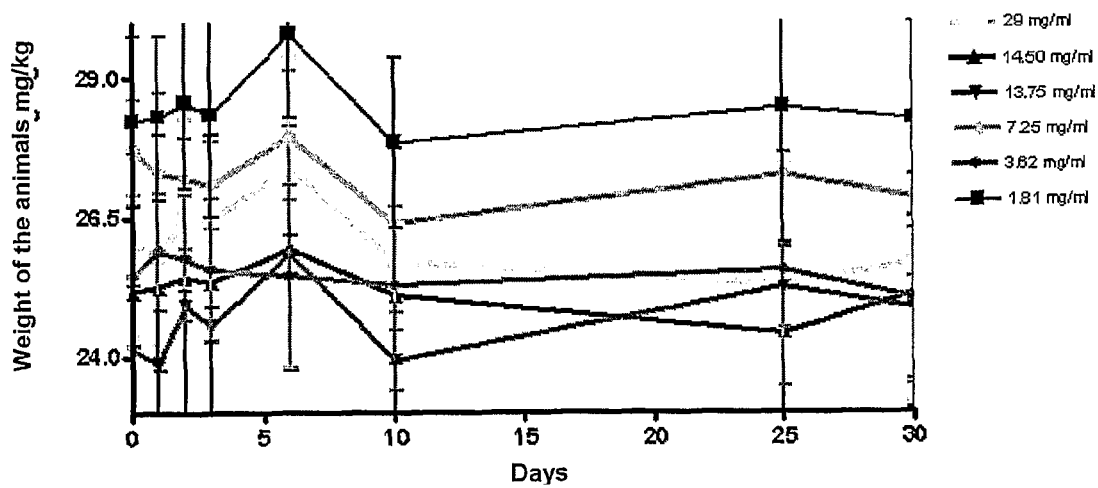
FIG. 22—Toxicology of monosodium compound administered to Balb-c mice by the endovenous route.

Our results (FIG. 22) have shown that the 14 mg/Kg dose corresponds to the 50% lethal dose ($DL_{50}$) as well as it was also, by the same administration route, the maximum tolerable dose. After necropsy, at Day 30, no significant macroscopic and hystopathologic alterations were observed for the internal organs.

After data analysis, for the in vivo antitumoral activity and toxicity previously described, a short comparative may be established between the action of the penta-1,4-dien-3-ones and their derivatives and the drugs presently used in the therapeutics, such as doxorubicin, taxol, and etoposide. The following Table lists these comparisons.

| ANTITUMORAL COMPOUND | DOSE | LETAL DOSE 50% |
|---|---|---|
| Doxorubicin | 60 to 75 mg/m² | 20 mg/kg |
| Taxol | 135 to 175 mg/m² | 400 mg/kg |
| Etoposide | 50 to 100 mg/m² | 59 mg/kg |
| DM-2 | 1.9 μg/mL* | 700 mg/kg |

*Different units from the others as the data had been obtained by preclinic experimental models instead of standard dose calculation obtained in humans, as presented by the drugs of the therapeutic.

The DM-1 compound presents an inferior $LD_{50}$ value as compared to those exhibited by taxol (1.75 fold smaller) and by doxorubicin (35 fold smaller).

During preclinic tests, DM-1 has not present any suggestive effect of acute respiratory and cardiac toxicity, what represents a great advantage to explore the series of compounds as potential antitumoral drugs with smaller antitumoral side effects.

It should be emphasized that the mentioned compounds may be also used as treatment and prophylaxis for neoplastic diseases caused by lung cancer, breast carcinoma, and multiple drugs resistant breast cancer, non-melanoma skin cancer, lymphoid leukemia, acute and chronic myeloid leukemia, erythroleukemia, myelodysplasias, colonic, ovarian, cervices, renal, pancreatic, prostatic cancer, soft tissue sarcomas, hepatocarcinomas, osteosarcomas, cancer of the central nervous system, neuroblastomas, astrocytomas, oropharyngeal, thyroid, gastric, and male reproductive apparatus.

Example 10

Hystological Description

Animals are sacrificed by cervical displacement and the organ fragments were collected from the areas next to the tumoral region, stored in vials containing 10% formaldehyde, and fixed to be submitted to the routine histological processing (PARDI, P C; SIMÕES, M J, BINIVIGNAT, G. O—Ultrastructural study of the remodeling of the stroma of persistent-estrous rats—Rev. Chil. Cienc. Méd. Biol 3(2):61-65, 1993).

Melanoma B16F10 cell line are implanted at 5×10⁴ cells per animal, the ideal dose to obtain the expected results and already proclaimed for this chosen type of animal.

All animals are treated after Day 14 of tumor implant and, as a result, the sequence of necropsis initiates at Day 15.

To visualize the results of HB-1 administration, animals are allocated into the following groups:

1—Control group, animals are identified from 1 to 6, treated with Miglyol 810® and kept under ad libitum feed and water;

2—HB-1 group, treated with HB-1 diluted in Miglyol 810®, kept under ad libitum feed and water.

In both cases, the standard administered dose is of 1.15 μg/kg, via intraperitoneal as the elicited administration route.

Animals are sacrificed by cervical displacement and necropsis is performed with the material immediately collected and transferred to vials containing 10% formaldehyde and, after a 1 to 2 day period, submitted to a routine histological technique Hystology Technique Manual (Manual De Técnicas Para Histologia—Normal E Patológica: Castro De Tolosa, Rodrigues, Behmer E Freitas Neto, Editora Manole 2003).

This technique consists of dehydration of the pieces with increasing alcohol concentrations, followed by diaphanization by xylol, impregnated with liquid paraffin at 57° C. in stove, and finally the blocks are embedded in paraffin at room temperature.

Block sectionings are performed by a semi-authomatic LEICA microthome, with 7 μm maximum thickness.

After cutting, the material is maintained in a water-bath to be transferred to glass thin plates previously coated with albumine, for material fixation.

After the fixation procedure to the thin plate, the hematoxylin/eosin staining method—Hystology Technique Manual (Manual (Manual De Técnicas Para Histologia—Normal E Patológica: Castro De Tolosa, Rodrigues, Behmer E Freitas Neto, Editora Manole 2003). is applied as it presents good results for tissue and cell morphologic evaluation, mainly to the components in each block.

Staining is performed as follows:
thin plate drying in stove at 57° C. for around 20 minutes;
cut diaphanization in two xylol baths;
hydration in decreasing alcohol amounts (100%, 96%, 70%, 50%);
wash in destined water for 30 minutes;
hematoxylin staining for 30 seconds followed by washing in running tap water to remove stain excess;
eosin staining for 1 minute;
dehydration with increasing alcohol amount (96%, 100%);
diaphanization in xylol (two baths).

After staining, the thin plates are mounted, then analysed by a ZEISS microscopy with a AXIOCAM-MRC3 trade mark digital camera, and the resulting pictures processed by a AXIOVISON REL 4.2 (Carl Zeiss Inc.) software, registered by a computer.

Hystological observations and results are illustrated as follows:

Result A: Control Group—Miglyol 810® Administration.

Figure 23:
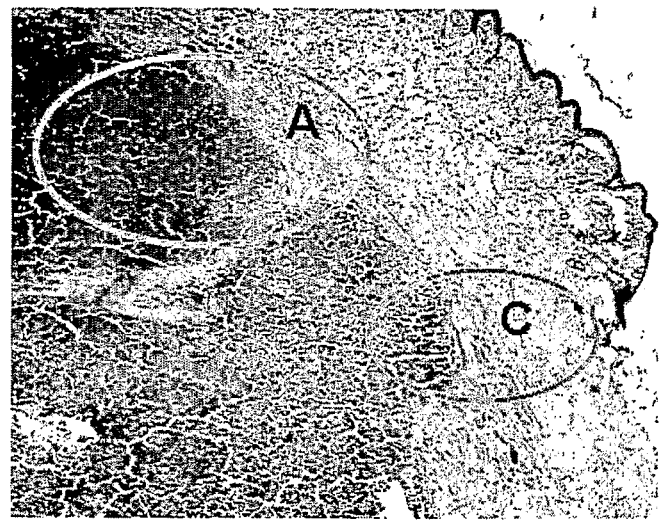
FIG. 23—Photomicrography of the dorsal melanoma tumor.
A—Presence of nodular pigmented dorsal tumor.
C—Presence of nodular pigmented dorsal tumor with absence of leukocytic inflammatory infiltrate.
Figure 24:
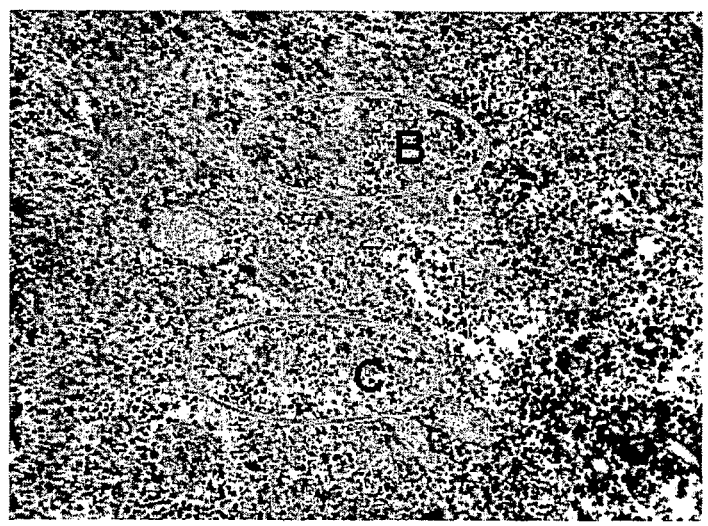
FIG. 24—Photomicrography of the dorsal melanoma tumor.
B—Presence of nodular pigmented dorsal tumor with great areas of necrosis.
C—Presence of nodular pigmented dorsal tumor with absence of infiltrate inflammatory leukocytes.

FIGS. 23 and 24 are shown the fragments of the tumoral tissue from control group: dorsal tumor implanted in C57BL/6J mice treated with Miglyol 810® diluent administered by the intraperitoneal route and sacrificed on Day 14 of treatment.

By the micrographies correspondent to FIGS. 23 and 24, we can observe the presence of nodular, pigmented dorsal tumor (A), with big necrosis area (B), and absence of leucocytic inflammatory infiltrate (C).

Result B: HB-1 Group—Diluted in Miglyol 810®.

Figure 25:
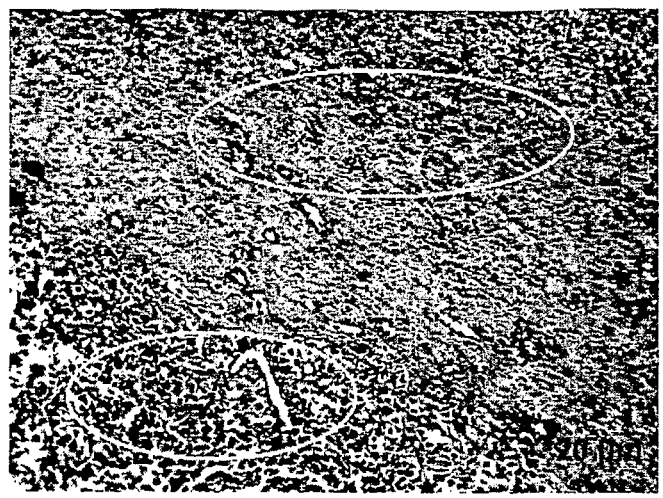
FIG. 25—Photomicrography of the melanoma dorsal tumor implanted in C57BL/6J mice after 14 days of treatment with HB-1 compound diluted in Miglyol 810® administered by the intraperitoneal route.
A—Presence of intense infiltrate inflammatory leukocytes on the intra- and peritumoral portions.
Figure 26:
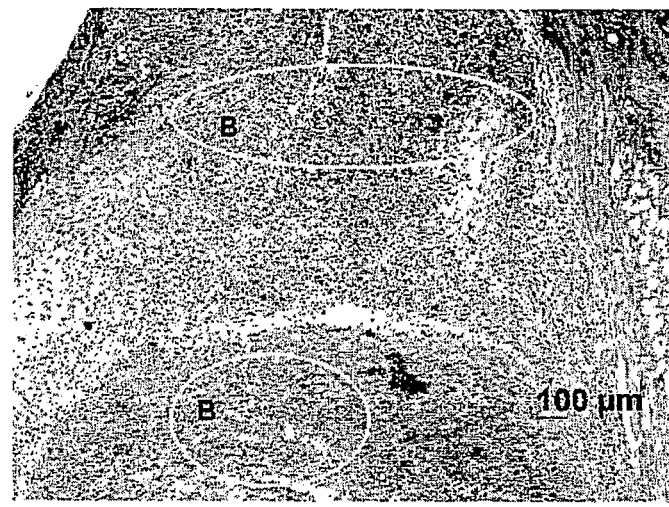
FIG. 26—Photomicrography of the implanted melanoma dorsal tumor in C57BL/6J mice after 14 days of treatment with HB-1 compound diluted in Miglyol 810® administered by the intraperitoneal route.

The histopathology analysis of dorsal tumors from the animals bearing melanoma treated with HB-1 diluted in Miglyol 810® is shown in FIGS. 25 and 26.

One can observe the presence of intense leukocytic inflammatory infiltrate in the intra- and peritumoral portions (A); nodular tumoral mass infiltrated and with extensive necrosis areas (B).

The presence of a leukocytic infiltrate in the peri- and intratumoral portions demonstrates that the 14 day treatment with HB-1 compound is able to induce a specific immune response, generated by the interaction between the compound and the tumoral cells or, indirectly, by the interactions with other cellular types. This inflammatory infiltrate present in the melanoma tumor treated with HB-1 compound was not found in the control group, which received the vehicle (Miglyol-810®) of the compound, in the same experimental conditions and by the same administration route. On the other hand, these findings corroborate the antitumoral efficacy of the HB-1 compound to inhibit tumoral cell growth and dissemination; no metastatic lesions were found in the treated animal group, when compared to the control group, in which several lesions or tumoral nodules were found in the lung and lymphatic ganglia.

Result C: Control Group—Diluted in Miglyol 810®.

Hystopathological analysis of the dorsal tumors of animals bearing melanoma treated with Miglyol 810® is shown in FIGS. 27 and 28.

Nodular, pigmented dorsal tumor (A), vascularized (*) and with great necrosis areas (B and D), and absence of intra- and peritumoral leukocytic inflammatory infiltrate (C).

Result D: Lung Parenchyma Metastasis

Hystopathological analysis of lung parenchyma metastasis is shown in FIGS. 29 and 30.

No alterations of thickness or bronchium epithelium rupture, changes of congestion or fibrin deposition and pigmented substances as well as the presence of inflammatory infiltration in the animals treated with HB-1 compound were observed (FIG. 29) as compared to the control group (FIG. 30). The presence of metastatic masses or nodules was not observed (FIG. 29). On the other hand, animals of the control group have shown several metastatic lesions next to the lung capsule containing tumoral cells in melanin pigment, without the presence of an inflammatory infiltrate (A).

Result E: Hystopathology Analysis of Internal Organs.

Hystopathology results of the internal organs, such as liver and kidneys, are shown in FIGS. 31 and 32, respectively. The results show preserved normal parenchymas, without sequels or inflammatory processes considerable. In FIG. 31, we can observe well-preserved hepatocytes, with well-defined lobuli and trabeculae in a radial pattern. It can be also observed that the central vein is well-preserved with typical sinusoids. In FIG. 32 are evident typical well-preserved kidney corpuscles, distal and proximal convulated tubules also well-preserved, not showing any strutural alteration.

The internal organs of the animals bearing dorsal melanoma and treated with Miglyol 810® diluent are normal in all cuts, without inflammatory processes or infiltrated or any other type of change that could be correlated to toxic effects or deposition of the diluent in the adjacent areas or tumoral mass.

Part 3

Antiparasite Activity

The present invention refers also to antiparasite action for the above mentioned derivatives listed in the Figures of Part 1 of this item.

The compounds here presented have been evaluated as for their in vitro effects on proliferation and/or viability of promastigote forms of different isolates from Leishmania spp causative of American tegumental leishmaniasis and on proliferation and/or viability of amastigote-like forms of Leishmania amazonensis.

The assays to measure inhibition of proliferation are performed by incubating different concentrations of the compounds ranging from 100.00-3.12 µg/mL and parasite number between $1.0 \times 10^6$ to $2.0 \times 10^6$ per milliliter of the culture medium to achieve total volumes between 2 and 20 mL of culture, as required for the experiment. Compounds are solubilized with dimethyl sulfoxide (DMSO) to produce a stock solution from which samples with different concentrations are obtained, by adding the culture medium in sufficient volume as required to attain the first desired concentration with the other concentrations being obtained by serial dilution of this first one, at ratio 2. The cultures are incubated at 22° C. or 34° C. for promastigotes and amastigotes, respectively.

As a positive control for parasite viability evaluation, only culture medium and parasite, without any other addition, were used. As toxicity control for the solvent present in compound composition, parasite forms were incubated with DMSO diluted in culture medium.

To quantify the promastigotes, Neubauer chambers are used and the cultures are quantified every 24 hours throughout the incubation period scheduled for each experiment. The samples are prepared from an initial dilution of 20 µL of the culture into 180 µL of the saline solution formulated (PBS+2% formaldehyde) to obtain a 1/10 dilution. Whenever necessary, serial dilutions may be performed from the first dilution. For all experiments, parasite forms should be incubated with several HB-1 concentrations, its respective controls with DMSO (we should have in mind that the initial HB-1 stock solution was prepared with DMSO and that its toxicity in relation to the parasite forms have to be assessed) and the normal culture, without any component additioned to the medium. Countings are performed as duplicates, by two different people and the final result is expressed as the arithmetic average from the two countings. The same procedure is employed to quantify the amastigote forms.

Compounds have exhibited good inhibitory profiles to promastigote proliferation since the first 24 hour of culture and at different culture medium.

The compounds were also very promising face to the inhibitory proliferative capacity of amastigotes-like, with these forms being extremely sensitive to the compounds. In the first 48 hours of incubation, 100% of the parasite turned into nonviable forms by all assayed concentrations of the compounds and, already in the first 24 hours, the 10 µg/mL and 20 µg/mL concentrations inhibited the cellular activity of 100% of the amastigotes.

This result is extremely relevant, since this intracellular form is the target established for the antiparasite agents in the treatment of human infections.

Viability and/or cellular proliferative assays of promastigote and amastigote forms are also performed by the MTT (diphenyl tetrazolium 3-[4,5-dimethylthiazol-2il]2,5-bromide) method as described by Moreira, et al. (Moreira, M. E. C., Del Portillo, H. A., Milder, R. V., Balanco, J. M. F. and Barcinski, M. A. Heat shock induction of apoptosis in promastigotes of the unicellular organism *Leishmania* (*Leishmania*) *amazonensis*, J. Cell Physiol 167, 305-313, 1996), modified.

After incubation of parasitic forms with the compounds, as described above, for predetermined periods of time for each experiment (24, 48, 72 hours, etc.), an 1.0 mL aliquot of cellular suspension is collected from each culture tube or vial and transferred to microcentrifuge tubes, where they are centrifuged at 14.000 rpm for 3 minutes, the culture medium is aspirated and discharged. To the sedimented cells are add 200 µL of PBS. After that, the volume in PBS of the cellular suspensions is splitted into two wells (duplicates of 100 µL each) of a 96 well culture plate. To each duplicate, 20 L of MTT (5 mg/mL stock solution, 1.0 mg/mL of final concentration) are added. After 1 h or 1 h 30 min, at a temperature of 22° C. (promastigotes) or 34° C. (amastigotes), 100 µL of 10% SDS are added to each well to interrupt the reaction, to lyse the cells and to dissolve the formazan crystals, resulting in an homogeneous blue solution appropriate to the absorbance measure by a spectrophotometer for culture microplates (3550 BIORAD model, Richmond, Calif.), at 595 nm as test wavelength and 690 nm as the reference wavelength.

The optical density (O.D.) values correspond to MTT enzymatic reduction by the metabolic active cells. Consequently, the O.D. is directly proportional to the number of viable cells of the cellular suspension. The progressive increase of O.D. indicates cellular proliferation. Results are expressed as arithmetic average of the optical density duplicates.

Blanks of reaction are obtained by incubating of the specific medium employed in each assay, in addition to MTT, and different HB-1 concentrations. The brownish-yellow color of HB-1 exerts certain interference on the colorimetric assay at different magnitudes, according to the medium and to HB-1 concentration. In general the O.D. blank ranged among assays from 0.002 to 0.020.

Observed activities and results are next illustrated:

Example 11

Effect of HB-1 Compound on Promastigote Form Proliferation of *Leishmania* (L) *amazonensis* in Warren Culture Medium Promastigote forms of *Leishmania* (L) *amazonensis* (isolate LV79, $8^{th}$ passage for the culture medium, day 7 of culture, stationary phase) are incubated in a proportion of $10^6$ promastigotes/mL in Warren medium, 3.0 mL final volume, in the presence of different concentrations of HB-1 and of the respective controls in equivalent volume of DMSO and culture medium, as positive control for proliferation and viability. The effect of HB-1 on the promastigotes of *Leishmania amazonensis* cultivated in Warren medium is shown in the next Table and FIG. 33.

EV: represents the individual control of each HB-1 concentration obtained by parasite incubation in a medium containing the volume of DMSO equivalent to that employed to obtain different final concentrations of HB-1, respectively.

As can be observed in the following Table and in FIG. 33, all HB-1 (from 100 µg/mL to 3.12 µg/mL) concentrations inhibit promastigote proliferation, in different proportions, from the first 24 hours of culture. Concentrations of 25 µg/1 mL, 50 µg/mL, and 100 µg/mL inhibit, respectively, 81%; 95.8%, and 100%, of parasite proliferation after 72 hours of incubation and achieve 100% of inhibition at 120 hours of culture.

| | N°. of promastigotes/mL ($\times 10^6$) Incubation time (hours) | | | | | |
|---|---|---|---|---|---|---|
| | 0 | 24 | 48 | 72 | 96 | 120 |
| HB-1 concentration (µg/mL) | | | | | | |
| 0 (control) | 1.0 | 4.05 | 9.46 | 11.5 | 12.3 | 20.0 |
| 100 | 1.0 | 1.15 | 0.2 | 0 | 0 | 0 |
| 50 | 1.0 | 2.1 | 0.4 | 0.1 | 0 | 0 |
| 25 | 1.0 | 3.25 | 1.8 | 0.4 | 0.1 | 0 |
| 12.5 | 1.0 | 2.55 | 2.25 | 3.9 | 5.9 | 18.3 |
| 6.25 | 1.0 | 2.5 | 3.95 | 7.15 | 13.0 | 18.6 |
| 3.12 | 1.0 | 3.0 | 5.95 | 10 | 11 | 17 |
| Equivalent volume of DMSO (EV) | | | | | | |
| 100 | 1.0 | 3.0 | 4.8 | 9.9 | 11.9 | 19.0 |
| 50 | 1.0 | 2.75 | 4.7 | 9.0 | 9.4 | 18.0 |
| 25 | 1.0 | 4.7* | 4.0 | 7.4 | 9.6 | 19.0 |
| 12.5 | 1.0 | 2.8 | 5.0 | 8.3 | 9.7 | 17.0 |
| 6.25 | 1.0 | 2.4 | 5.25 | 6.55 | 10.5 | 18.5 |
| 3.12 | 1.0 | 3.0 | 4.2 | 5.9 | 10.8 | 20.0 |

Therefore, within this period, a 100% of the parasites are dead. Consequently, we verify that, at the experimental condition above reported, the effective concentrations of HB-1 to produce 100% inhibition of promastigote proliferation (=100% mortality) are related to the time of incubation. Therefore, 100% mortality is achieved in 120 hours or in 96 hours or in 72 hours of culture, when HB-1 concentrations are 25 µg/mL, 50 µg/mL, or 100 µg/mL, respectively. Concentrations from 12.5 µg/mL to 3.12 µg/mL have turned out to be sub-lethal, because proliferation inhibition is present up to 72 hours of cultivation.

Example 12

Effect of HB-1 Compound on *Leishmania* (L) *amazonensis* Promastigotes in RPMI Culture Medium

*Leishmania* (L) *amazonensis* promastigote forms (isolate LV79, $1^{st}$ passage in culture medium, day 7 of culture, stationary phase) are incubated at a proportion of $10^6$ promastigotes/mL of RPMI medium, 3.0 mL final volume, in the presence of different concentrations of HB-1 and of the respective controls in DMSO. The effect of HB-1 compound on the proliferation of *Leishmania* (L) *amazonensis* promastigotes-RPMI medium is shown in the next Table and in FIG. 34.

|  | N°. of promastigotes/ mL (×10$^6$) Incubation time (hours) | | | | |
|---|---|---|---|---|---|
|  | 0 | 24 | 48 | 72 | 144 |
| HB-1 concentration (µg/mL) | | | | | |
| 0 (control) | 1.0 | 2.0 | 2.8 | 3.4 | 3.3 |
| 100 | 1.0 | 0 | 0 | 0 | 0 |
| 50 | 1.0 | 0.1 | 0 | 0 | 0 |
| 25 | 1.0 | 0.5 | 0 | 0 | 0 |
| 12.5 | 1.0 | 0.7 | 0 | 0 | 0 |
| 6.25 | 1.0 | 0.8 | 1.0 | 0.7 | 0.3 |
| 3.12 | 1.0 | 1.6 | 2.1 | 2.1 | 2.4 |
| Equivalent volume of DMSO (EV) | | | | | |
| 100 | 1.0 | 1.5 | 2.6 | 2.7 | 3.0 |
| 50 | 1.0 | 2.1 | 2.1 | 2.8 | 2.7 |
| 25 | 1.0 | 1.7 | 2.2 | 2.7 | 3.0 |
| 12.5 | 1.0 | 1.7 | 2.5 | 2.7 | 3.0 |
| 6.25 | 1.0 | 1.8 | 2.1 | 2.8 | 2.5 |
| 3.12 | 1.0 | 1.9 | 2.3 | 2.6 | 3.0 |

EV: represents the individual control of each HB-1 concentration obtained by parasite incubation in a medium containing the volume of DMSO equivalent to that employed to obtain different final concentrations of HB-1, respectively.

We can observe that the HB-1 compound is able to inhibit the proliferation of Leishmania promastigotes in all concentrations employed (from 100 µg/mL to 3.12 µg/mL), when the culture medium used is RPMI. The inhibitory effect is particularly conspicuous at these experimental conditions. As shown by the previous Table and FIG. 34, since the first 24 hours of culture, there is an important inhibitory effect of HB-1 with all tested concentrations and, at 48 hours of culture, we can observe 100% of inhibitory effect (=100% mortality) with concentrations from 100 µg/mL to 12.5 µg/mL.

Example 13

Determination of Viability for the Prosmatigote Form of Leishmania (L) amazonensis Treated with HB-1, in RPMI Culture Medium In this assay, viability of the promastigote form Leishmania is assessed by the MTT method, when incubated in RPMI medium, in the presence of HB-1 or of its respective controls in DMSO. It is also possible to verify if the effect of HB-1 could be detected in the stationary phase of the growth curve.

For the incubations, promastigotes of the LV79 isolate, in 1$^{st}$ passage and in Day 7 of culture, are employed, from a 1.0×10$^6$/mL as initial inoculum. The final reaction volume is of 3.0 mL. The results of the viability determination for the promastigote forms of Leishmania (L) amazonensis treated with HB-1 in RPMI medium are shown in the next Table and in FIG. 35.

|  | Optical Density 595/690 nm (average value from duplicates) Time of incubation (hours) | | | |
|---|---|---|---|---|
|  | 24 | 48 | 72 | 144 |
| HB-1 concentration(µg/mL) | | | | |
| 0 (control in RPMI) | 0.067 | 0.080 | 0.074 | 0.031 |
| 100 | 0.016 | 0.012 | 0.011 | 0.011 |
| 50 | 0.008 | 0.004 | 0.005 | 0.005 |
| 25 | 0.004 | 0.005 | 0.002 | 0.005 |
| 12.5 | 0.010 | 0.004 | 0.003 | 0.005 |
| 6.25 | 0.039 | 0.033 | 0.044 | 0.031 |
| 3.12 | 0.062 | 0.085 | 0.104* | 0.021 |
| Equivalent volume of DMSO (EV) in RPMI | | | | |
| 100 | 0.079 | 0.096* | 0.077 | 0.037 |
| 50 | 0.074 | 0.082 | 0.048 | 0.027 |
| 25 | 0.081* | 0.082 | 0.049 | 0.026 |
| 12.5 | 0.076 | 0.079 | 0.046 | 0.030 |
| 6.25 | 0.073 | 0.071 | 0.041 | 0.021 |
| 3.12 | 0.071 | 0.080 | 0.051 | 0.024 |

*likely a quantification distortion (technical error).

EV: represents the individual control of each HB-1 concentration obtained by parasite incubation in a medium containing the volume of DMSO equivalent to that employed to obtain different final concentrations of HB-1, respectively.

The results presented in the previous Table and in FIG. 35 show that, since the first 24 hours of incubation, all HB-1 concentrations between 6.25 µg/mL and 100 µg/mL irreversibly compromise cell viability, because as there is no evidence of recovery in latter times of incubation.

By means of mitochondrial activity observation, measured by MTT at 144 hours of incubation, from the comparison between the reaction control (without HB-1) and the other reactions, we could clearly demonstrate that HB-1 acts making the cells nonviable both in the exponential phase and in the stationary phase of the growth curve.

These analyses corroborate the results obtained by means of Neubauer chamber quantification. We can observe that HB-1 in concentrations above 12.5 µg/mL has a clear leishmanicidal effect, inasmuch as the cells do not recover throughout the growth curve. The 6.25 µg/mL concentration reveals a leishmaniostatic effect; however, incapable of making 100% of the promastigote forms nonviable. The effect of HB-1 on mitochondrial activity may be observed both in the exponential and in the stationary phase of parasite growth.

Example 14

Assessment of the HB-1 Effect on Leishmania Isolates Causing Localized Cutaneous Leishmaniasis (L.C.L.) and Diffuse Cutaneous Leishmaniasis (D.C.L.) by the MTT Method This experiment is developed in the Warren medium using an initial inoculum of 2.0×10$^6$/mL of the medium for the isolates. Cultures were at the day 7$^h$ of passage and at the final exponential phase growth (day 6 of incubation). The results of viability determination for the Leishmania (isolate L.C.L.) promastigotes, incubated in Warren medium and in the presence of HB-1, are shown in the next Table and in FIG. 36. The culture final volume is of 5 mL and the MTT reactions are processed in 1 h and 30 minutes of incubation, beginning with 1.0 mL of culture.

| HB-1 concentration or equivalent volume of DMSO | TIME OF INCUBATION (hours) | | | |
|---|---|---|---|---|
| | 24 O.D.* | 48 O.D. | 72 O.D. | 96 O.D. |
| 0 (normal culture control) | 0.719 | 1.416 | 3.618 | 3.779 |
| HB-1 20 µg/mL | 0.056 | 0.014 | 0.012 | 0.012 |
| HB-1 10 µg/mL | 0.177 | 0.153 | 0.176 | 0.187 |
| HB-1 5 µg/mL | 0.489 | 0.452 | 1.346 | 1.834 |
| DMSO - EV 20 µg/mL | 0.718 | 1.315 | 2.763 | 3.374 |
| DMSO - EV 10 µg/mL | 0.737 | 2.238 | 3.612 | 3.631 |
| DMSO - EV 5 µg/mL | 0.710 | 2.247 | 3.537 | 3.476 |

*O.D. = optical density at 595/690 nm wavelength (average of duplicates)
EV: individual control of each HB-1 concentration obtained by parasite incubation in a medium containing equivalent volume of DMSO.

As shown by the previous Table and by FIG. 36, the L.C.L. isolate is extremely susceptible to HB-1 action. The effect of this compound on the cells is clearly dose-dependent so that the 5 µg/mL concentration cause only a partial inhibition of proliferation, the concentration of 10 µg/mL has a leishmaniostatic effect, and the 20 µg/mL concentration is leishmanicide.

In the next Table and in FIG. 37 are shown the results of viability determination for the promastigotes of *Leishmania* (isolate D.C.L.) incubated in Warren medium in the presence of HB-1.

| HB-1 concentration or equivalent volume of DMSO | TIME OF INCUBATION (hours) | | | |
|---|---|---|---|---|
| | 24 O.D.* | 48 O.D. | 72 O.D. | 96 O.D. |
| 0 (normal culture control) | 0.645 | 1.880 | 3.221 | 3.189 |
| HB-1 20 µg/mL | 0.025 | 0.012 | 0.016 | 0.013 |
| HB-1 10 µg/mL | 0.083 | 0.059 | 0.017 | 0.016 |
| HB-1 5 µg/mL | 0.299 | 0.682 | 0.785 | Erro** |
| DMSO - EV 20 µg/mL | 0.623 | 1.335 | 2.454 | 3.267 |
| DMSO - EV 10 µg/mL | 0.332 | 1.327 | 2.892 | 2.977 |
| DMSO - EV 5 µg/mL | 0.422 | 1.422 | 3.027 | 3.367 |

*O.D. = optical density at 595/690 nm wavelength.
**point excluded from the analysis due to methodologic error.
EV: represents the individual control of each HB-1 concentration obtained by parasite incubation in a medium containing the volume of DMSO equivalent to that employed to obtain different concentrations.

In relation to the D.C.L. isolated, the results are similar (previous Table and FIG. 37), showing a clear effect of HB-1 on promastigote viability. However, in this case, parasites seem to be more sensitive to the compound, because from the 10 µg/mL we can observe the leishmanicide effect, whereas for L.C.L. the effect of the compound at this dose was only leishmaniostatic.

Example 15

Assessment of HB-1 Effect on Amastigote-Like Forms of *Leishmania* (L) *amazonensis*

Considering that the amastigote forms are those that multiply inside a vertebrate host and, consequently, are responsible for the disease, it is indispensable to evaluate the viability of these forms when incubated with HB-1.

This evaluation is performed as previously described and by applying the amastigote forms obtained from an axenic culture. The results are shown in the next Table:

| HB-1 concentration or equivalent volume of DMSO | TIME OF INCUBATION (hours) | | |
|---|---|---|---|
| | 24 O.D.* | 48 O.D. | 72 O.D. |
| 0 (normal culture control) | 0.428 | 0.772 | 1.402 |
| HB-1 20 µg/mL | 0.009 | 0.012 | 0.016 |
| HB-1 10 µg/mL | 0.010 | 0.014 | 0.014 |
| HB-1 5 µg/mL | 0.16 | 0.012 | 0.012 |
| DMSO - EV 20 µg/mL | 0.149 | 0.177 | 0.199 |
| DMSO - EV 10 µg/mL | 0.319 | 0.410 | 0.694 |
| DMSO - EV 5 µg/mL | 0.212 | 0.507 | 0.916 |

*O.D. = optical density
EV: represents the individual control of each HB-1 concentration obtained by parasite incubation in a medium containing the volume of DMSO equivalent to that employed to obtain different final concentrations of HB-1, respectively.

As shown by the previous Table, the amastigote forms turned out to be extremely sensitive to HB-1. In the first 48 hours, 100% of the parasites become nonviable by all assayed HB-1 concentrations and, since the first 24 hours, the 10 µg/mL and 20 µg/mL concentrations inhibit the cellular activity of 100% of the amastigotes.

It should be emphasized that the mentioned compounds may also be used to treat human and/or animal parasitoses caused by tissue, blood, intestinal protozoan and protozoan like *Leishmania, Plasmodium, Trypanosoma, Toxoplasma, Giardia, Entamoeba* genera and outhers helmintic parasite like *Taenia, Schistosoma, Ancylostoma, Necator, Ascais, Enterobius, Wuchereia* genera, in their different clinical manifestations.

The invention claimed is:

1. A method of making a compound of structure II,

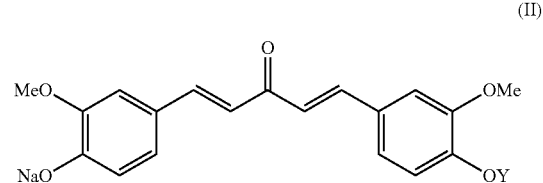

(II)

wherein, Y is selected from the group consisting of hydrogen, and sodium;
which comprises contacting a compound of structure I,

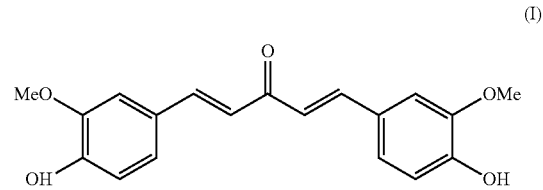 [SMILES: COc1cc(/C=C/C(=O)/C=C/c2ccc(O)c(OC)c2)ccc1O]

(I)

with a metallic alkoxide of the formula ROM, wherein M is sodium,
wherein the molar ratio of the compound of structure I and ROM is between 1:1 and 1:2 in the presence of an alcohol ROH solvent.

2. The method of claim 1, ROM is sodium ethoxide, which further comprises solvent rotoevaporation until the formation of a solid.

3. The method of claim 1, wherein resulting monosodium and/or disodium salts are passed through a sieve in order to obtain a fine powder that may be solubilized without difficulty in water and employed in biological tests.

4. A compound selected from the group consisting of sodium 4-[5-(4-hydroxy-3-methoxy-phenyl)-3-oxo-penta-1,4-dienyl]-2-methoxy-phenolate; and 3-oxo-penta-1,4-dienyl-bis(sodium 2-methoxy-phenolate).

5. A pharmaceutical composition for treating melanoma or a parasitic disease comprising a compound selected from the group consisting of structure II and a compound of claim 4, wherein structure II is:

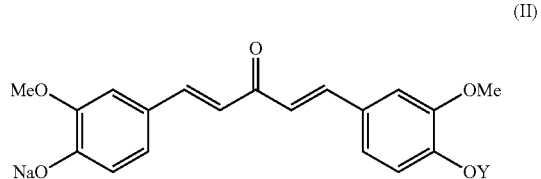

(II)

wherein Y is selected from the group consisting of hydrogen, and sodium.

6. The pharmaceutical composition of claim 5, further comprising a pharmaceutically acceptable carrier which is formulated for intramuscular, subcutaneous, intraperitoneal, endovenous or oral administration.

7. The pharmaceutical composition of claim 5 wherein said parasitic disease results from infection of a parasite selected from the group consisting of tissue, blood and intestinal protozoa comprising *Leishmania, Plasmodium, Trypanosoma, Toxoplasma, Giardia*, or *Entamoeba* genera, in addition to helmynthic infections caused by *Taenia, Schistosoma, Ancylostoma, Necator, Ascaris, Enterobius* or *Wuchereria* genera.

8. The pharmaceutical composition of claim 5 wherein said composition exhibits activity selected from the group consisting of proliferative activity of a promastigote form of *Leishmania* (L) *amazonensis* in Warren media, proliferative activity of the promastigote form of *Leishmania* (L) *amazonensis* in RPMI media, activity on the viability of the promastigote forms of *Leishmania* (L) *amazonensis* treated with HB-1, in RPMI medium, activity on *Leishmania* isolates causative of localized cutaneous leishmaniosis (L.C.L.) and of diffuse cutaneous leishmaniosis (D.C.L.), by the MTT method, and activity on amastigote-like forms of *Leishmania* (L) *amazonensis*.

9. The pharmaceutical composition of claim 5 wherein said compound causes no significant alterations in any of the normal organs studied, no necrosis areas, pigmentation, or cellular alterations in application against cancer and parasitic diseases.

10. A pharmaceutical composition comprising DM-1-sodium 4-[5-(4-hydroxy-3-methoxy-phenyl)-3-oxo-penta-1,4-dienyl]-2-methoxy-phenolate)- and DM-2-disodium_3-oxo-penta-1,4-dienyl-bis(2-methoxy-phenolate)- compounds.

* * * * *